(12) United States Patent
Prajapati et al.

(10) Patent No.: US 12,361,165 B2
(45) Date of Patent: Jul. 15, 2025

(54) SECURITY MANAGEMENT OF HEALTH INFORMATION USING ARTIFICIAL INTELLIGENCE ASSISTANT

(71) Applicant: MatrixCare, Inc., Bloomington, MN (US)

(72) Inventors: Adhiraj Ganpat Prajapati, St. Paul, MN (US); Samia Sadeque Alam, Houston, TX (US); Amy Ostrem, Maple Grove, MN (US); Kedar Mangesh Kadam, Nova Scotia (CA)

(73) Assignee: MatrixCare, Inc., Bloomington, MN (US)

( * ) Notice: Subject to any disclaimer, the term of this patent is extended or adjusted under 35 U.S.C. 154(b) by 415 days.

(21) Appl. No.: 18/062,813

(22) Filed: Dec. 7, 2022

(65) Prior Publication Data

US 2023/0214525 A1     Jul. 6, 2023

Related U.S. Application Data

(60) Provisional application No. 63/295,381, filed on Dec. 30, 2021.

(51) Int. Cl.
*G06F 21/62* (2013.01)
*G06F 21/32* (2013.01)
(Continued)

(52) U.S. Cl.
CPC .......... *G06F 21/6245* (2013.01); *G06F 21/32* (2013.01); *G16H 10/60* (2018.01);
(Continued)

(58) Field of Classification Search
None
See application file for complete search history.

(56) References Cited

U.S. PATENT DOCUMENTS 10,268,834 B2 * 4/2019 Pourzandi .............. H04L 9/008
11,100,933 B2 * 8/2021 Lefkofsky ............ G06F 16/332
(Continued)

FOREIGN PATENT DOCUMENTS

CN         113724695 A    * 11/2021
KR      20170073456 A    *  6/2017    ......... G06F 21/6245

OTHER PUBLICATIONS

Ciprian Chelba, Timothy J. Hazen, and Murat Saraclar; (Retrieval and Browsing of Spoken Content); pp. 11; Published on IEEE: May 2008.*

*Primary Examiner* — Ali H. Cheema
(74) *Attorney, Agent, or Firm* — Patterson + Sheridan, LLP

(57) ABSTRACT

Certain aspects of the present disclosure provide techniques for security management of health information using artificial intelligence assistant by receiving, at an artificial intelligence (AI) assistant device from a requestor in an environment, an utterance including a request to provide health information related to a patient and confirming, via a machine learning model hosted by the AI assistant device, whether an unauthorized person is present in the environment with the AI assistant device, where the unauthorized person is not permitted by the patient to receive the health information but is permitted to interact with the AI assistant device. Further, in response to determining that the unauthorized person is present, generating, by the AI assistant device, an audio deferral that does not include the health information that was requested.

17 Claims, 15 Drawing Sheets

(51) Int. Cl.
*G16H 10/60* (2018.01)
*G06F 3/16* (2006.01)
*G16H 40/20* (2018.01)
*G16H 40/67* (2018.01)

(52) U.S. Cl.
CPC ............ *G06F 3/165* (2013.01); *G16H 40/20* (2018.01); *G16H 40/67* (2018.01)

(56) References Cited

U.S. PATENT DOCUMENTS

| | | | | |
|---|---|---|---|---|
| 11,581,099 | B1* | 2/2023 | Rufo | G16H 20/13 |
| 2002/0116509 | A1* | 8/2002 | DeLaHuerga | A61J 7/0084 |
| | | | | 713/176 |
| 2004/0249778 | A1* | 12/2004 | Iliff | G16H 15/00 |
| | | | | 706/45 |
| 2005/0091338 | A1* | 4/2005 | de la Huerga | G07C 9/28 |
| | | | | 709/217 |
| 2008/0030764 | A1* | 2/2008 | Zhu | G06F 9/5038 |
| | | | | 358/1.15 |
| 2008/0283542 | A1* | 11/2008 | Lanka | G07F 17/0092 |
| | | | | 221/6 |
| 2013/0024382 | A1* | 1/2013 | Dala | H04L 63/0464 |
| | | | | 705/51 |
| 2018/0197624 | A1* | 7/2018 | Robaina | A61B 90/37 |
| 2019/0139539 | A1* | 5/2019 | Nuzzi | G06N 5/046 |
| 2020/0118680 | A1* | 4/2020 | Rao | G16H 20/10 |
| 2020/0175961 | A1* | 6/2020 | Thomson | G10L 15/28 |
| 2021/0031724 | A1* | 2/2021 | Hallberg | G06F 21/82 |
| 2021/0193154 | A1* | 6/2021 | Zhang | G06F 3/165 |
| 2021/0240720 | A1* | 8/2021 | Muse | G06F 16/9537 |
| 2022/0262474 | A1* | 8/2022 | Kamen | G16H 20/10 |
| 2023/0335250 | A1* | 10/2023 | Kamen | A61M 5/1417 |
| 2023/0355995 | A1* | 11/2023 | Forsell | A61B 5/0031 |
| 2024/0004887 | A1* | 1/2024 | Zimmermann | G06F 16/24578 |

* cited by examiner

SECURITY MANAGEMENT OF HEALTH INFORMATION USING ARTIFICIAL INTELLIGENCE ASSISTANT

CROSS-REFERENCE TO RELATED APPLICATIONS

This application claims benefit of U.S. provisional patent application Ser. No. 63/295,381 filed Dec. 30, 2021. The aforementioned related patent application is herein incorporated by reference in its entirety.

BACKGROUND

Field

Embodiments of the present disclosure relate to data security. More particularly, the present disclosure provides for the proper sharing of health information in a residential environment via an Artificial Intelligence (AI) assistant.

Description of the Related Art

In a closed healthcare environment, data control procedures can ensure the proper sharing and secret keeping of health information by restricting access of persons in the environment. For example, when sharing health information according to a doctor-patient relationship, only the doctor, the patient, and parties expressly permitted by the patient may be allowed in the room; keeping unauthorized persons out of the room so that health information is not shared with those persons who are not permitted to receive the health information in question. However, in a residential environment (such as a personal residence, a common area, or a group home), which is open to various persons, access restriction may not be possible, and more challenging data security measures may be required to ensure proper handling of health information.

SUMMARY

Certain embodiments provide a method that includes receiving, at an AI assistant device from a requestor in an environment, an utterance including a request to provide health information related to a patient and confirming, via a machine learning model hosted by the AI assistant device, whether an unauthorized person is present in the environment with the AI assistant device, where the unauthorized person is not permitted by the patient to receive the health information but is permitted to interact with the AI assistant device. The method also includes, in response to determining that the unauthorized person is present, generating, by the AI assistant device, an audio deferral that does not include the health information that was requested.

Certain embodiments provide a method that includes receiving, at an AI assistant device executing a local instance of machine learning model, a request for health information related to a patient from a requestor in an environment and, in response to determining via the machine learning model that the request is directed from the requestor to the patient or an authorized party to share the health information, waiting for a predefined time for a reply. The method also includes after the predefined time, in response to the patient or the authorized party not sharing the health information, confirming whether an unauthorized person is present in the environment with the AI assistant device via the machine learning model where the unauthorized person is not permitted by the patient to receive the health information, in response to confirming that the unauthorized person is not present in the environment, determining whether the reply included the health information requested by the request, and when the reply did not include the health information, generating an audio alert by the AI assistant device that includes the health information requested by the request.

Certain embodiments provide an AI assistant device that includes a processor and a memory including instructions for a machine learning model that when executed by the processor cause the processor to perform operations. The operations include receiving, at an AI assistant device from a requestor in an environment, an utterance including a request to provide health information related to a patient, determining, via the machine learning model, whether an unauthorized person is present in the environment with the AI assistant device, where the unauthorized person is not permitted by the patient to, and in response to determining that the unauthorized person is present, generating, by the AI assistant device, an audio deferral that does not include the health information that was requested.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure provide apparatuses, methods, processing systems, and computer readable mediums for proper sharing and secret keeping for security management of health information when using personal artificial intelligence (AI) assistant.

AI assistants provide a bevy of services to their users. These services can include responding to voice-activated requests (e.g., responding via audio to a request for the day's forecast with a local weather prediction), integrating with a human user's calendar, controlling appliances or lights, placing phone calls, or the like. These AI assistants often reside partially on a local device, as a local client, and partially in a back-end service located remotely (e.g., in a cloud server) from the local device. The local client handles data collection, some preprocessing, and data output, while the back-end service may handle speech recognition, natural language processing, and data fetching (e.g., looking up the requested weather forecast).

Some AI assistants may offer different levels of control for different users in a multi-user environments. For example, a first AI assistant may provide a first user (e.g., a parent) and a second user (e.g., a child) with the ability to turn the lights on or off via voice command, but only allow the first user to automatically change the thermostat. However, merely providing different access tiers does not offer sufficient protection for health information, as the source of the request does not indicate the potential recipients of such information. Accordingly, if the first user wishes to receive information related to a medical condition from the AI assistant, and not have the second user learn of this medical condition, the AI assistant should take additional care to ensure that the second user does not receive the associated health information. The present disclosure therefore provides for the proper sharing and secret keeping for health information when using personal AI assistants to improve data security, increase functionality in AI assistants, provide for better healthcare outcomes, and prophylactically improve treatment of medical conditions among other benefits.

Example Use Environment

Figure 1:
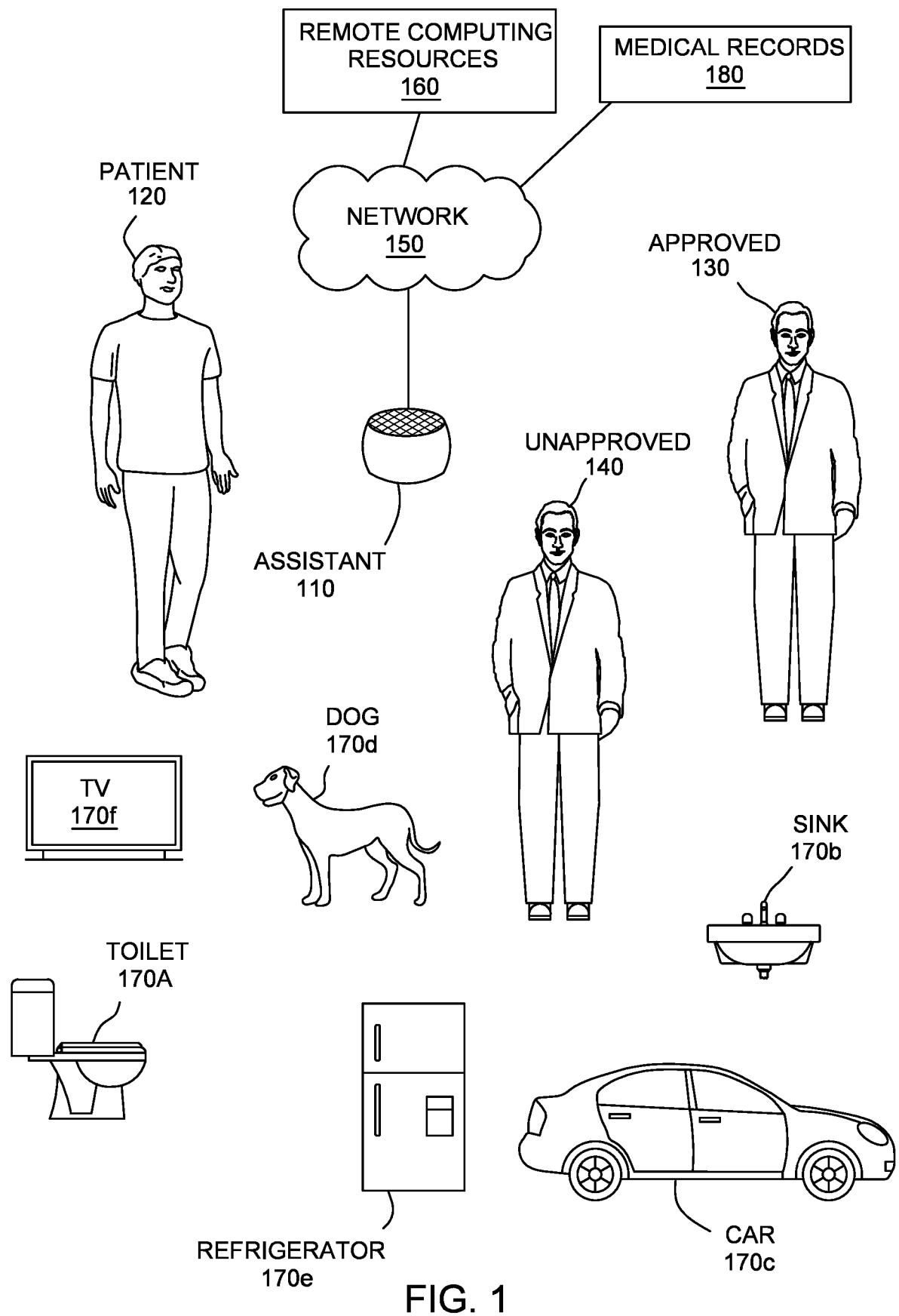
FIG. 1 illustrates an environment in which an assistant device, hosting a local client for an AI assistant, may be deployed to interact with various persons, according to embodiments of the present disclosure.

FIG. 1 illustrates an environment 100 in which an assistant device 110, hosting a local client for an AI assistant, may be deployed to interact with various persons, according to embodiments of the present disclosure. As discussed herein, the environment 100 is a residential environment, such as a personal home, a group home, a care facility, a community center, a car, a store, or other community area. Various persons may come and go in the environment 100 with different levels of access to health information. The environment 100 generally refers to the surrounding areas in which audio outputs of the assistant device 110 are comprehensible to a person of average hearing (unaided by listening devices), and the boundary of the environment 100 may be defined by a Signal to Noise Ratio (SNR) in decibels (dB) for output audio that may change as the volume of the assistant device 110 changes or as background noise changes.

In a healthcare context, the persons that an assistant device 110 may variously interact with include patients 120 whose health and well-being are monitored, authorized persons 130 who are currently authorized by the patients 120 to receive health information related to the patient 120 via the assistant device 110, and unauthorized persons 140 who are not currently authorized by the patients 120 receive health information related to the patient 120. In various embodiments, the authorized persons 130 and the unauthorized persons 140 may be permitted to interact with the assistant device 110 (or denied access to the assistant device 110) for non-healthcare related information independently of the permissions granted/denied for receiving health information related to the patient 120. Various other objects 170a-f (generally or collectively, objects 170) may also be present in the environment 100 or otherwise be observable by the assistant device 110 including, but not limited to: toilets 170a, sinks 170b, cars 170c, pets 170d, appliances 170e, audio sources 170f (e.g., televisions or radios), etc.

As used herein, a patient 120 may be one of several persons in the environment 100 to whom medical data and personally identifiable information (PII) pertain. Generally, a patient 120 is an authorized user for accessing their own data, and may grant rights for others to also access those data or to grant additional persons the ability to access these data on behalf of the patient 120 (e.g., via medial power of attorney). For example, a patient 120 may grant an in-home health assistant, a nurse, a doctor, a trusted relative, or other person the ability to access medical data and PII. A patient 120 may also revoke access to the medical data and PII, and may grant or revoke access to some or all of the data. Accordingly, a patient 120 is a person that the medical data and PII relate to, authorized persons 130 are those with currently held rights to access some or all of the medical data and PII, and unauthorized persons 140 include those who have not yet been identified as well as those currently lacking rights to access the medical data and PII. The identification and classification of the various persons is discussed in greater detail in relation to FIG. 2.

The assistant device 110 offers a user interface for requesting and receiving controlled access to health information. In some embodiments, the assistant device 110 is an audio-controlled computing device with which the users may interact with verbally, but various other devices may also be used as a user interface to request or provide health information to authorized parties in the environment. For example, a television may be used to output health information via a video overlay, a mobile telephone may be used to receive requests via touch-input and output health information via video or audio, etc. Generally, the assistant device 110 can be any device capable of hosting a local instance of an AI assistant and that remains in an "on" or "standby" mode to receive requests and provide outputs related to health information while remaining available for other tasks. For example, the assistant device 110 may also handle home automation tasks (e.g., controlling a thermostat, lights, appliances) on behalf of a user or interface with the television to provide health information while the patient 120 is watching a program. Example hardware for an assistant device 110 is discussed in greater detail in regard to FIG. 5.

In various embodiments, the assistant device 110 captures audio in the environment 100 and, to determine how to respond to the captured audio, may locally process the audio, may be in communication with remote computing resources 160 via a network 150 to process the audio remotely, or may perform some audio processing locally and some audio processing remotely. The assistant device 110 may connect to the network 150 via wired technologies (e.g., wires, fiber optic cable, etc.), wireless technologies (e.g., WIFI®, cellular, satellite, Bluetooth®, etc.), or combinations thereof. The network 150 may be any type of communication network, including data and/or voice networks, local area networks, and the Internet.

To determine how or whether to respond to audio captured in the environment, the assistant device 110 may need to filter out unwanted noises from desired audio, identify the source of the audio, and determine the content of the audio. For example, if the assistant device 110 detects audio of a request for the next scheduled doctor's appointment for the patient 120, the assistant device 110 may need to determine whether the request was received from an audio source 170f as unwanted noise (e.g., a character speaking in a movie or television program), the patient 120, an authorized person 130 (e.g., an in-home care assistant looking up care details for the patient 120), or an unauthorized person 140 (e.g., a curious visitor without authorization to receive that information from the assistant device 110). Other filters may be used to identify and discard sounds made by various other objects 170 in the environment 100.

In order to identify the content of the desired audio (e.g., a command to the assistant device 110), an audio recognition (AR) engine performs audio analysis/filtering and speech recognition on the captured audio signals and calculates a similarity between any audio identified therein and known audio samples (e.g., utterances for certain desired interactions). The AR engine then compares this similarity to a threshold and, if the similarity is greater than the threshold, the AR engine determines that a known audio cue has been received from the environment. The AR engine may use various types of speech and audio recognition techniques, such as, large-vocabulary speech recognition techniques, keyword spotting techniques, machine-learning techniques (e.g., support vector machines (SVMs)), neural network techniques, or the like. In response to identifying an audio cue, the assistant device 110 may then use the audio cue to determine how to next respond. Some or all of the audio processing may be done locally on the assistant device 110, but the assistant device 110 may also offload more computationally difficult tasks to the remote computing resources 160 for additional processing.

In various embodiments, the assistant device 110 may also access health records 180 via the network 150 or may store some health records 180 locally for later access. The health records 180 may include one or more of: medical histories for patients, upcoming or previous appointments, medications, personal identification information (PII), demographic data, emergency contacts, treating professionals (e.g., physicians, nurses, dentists), medical powers of attorney, and the like. The health records 180 may be held by one or more different facilities (e.g., a first doctor's office, a second doctor's office, a hospital, a pharmacy) that the assistant device 110 authenticates with to receive the data. In some embodiments, the assistant device 110 may locally cache some of these health records 180 for offline access or faster future retrieval. Additionally or alternatively, a patient 120 or authorized person 130 can locally supply the medical data, such as by requesting the assistant device 110 to "remind me to take my medicine every morning", importing a calendar entry for a doctor's appointment from a linked account or computer, or the like.

Additionally, the assistant device 110 may store identifying information to distinguish the patient 120, authorized persons 130, and unauthorized persons 140 when deciding whether to share the health records 180 or data based on the health records 180.

Figure 2:
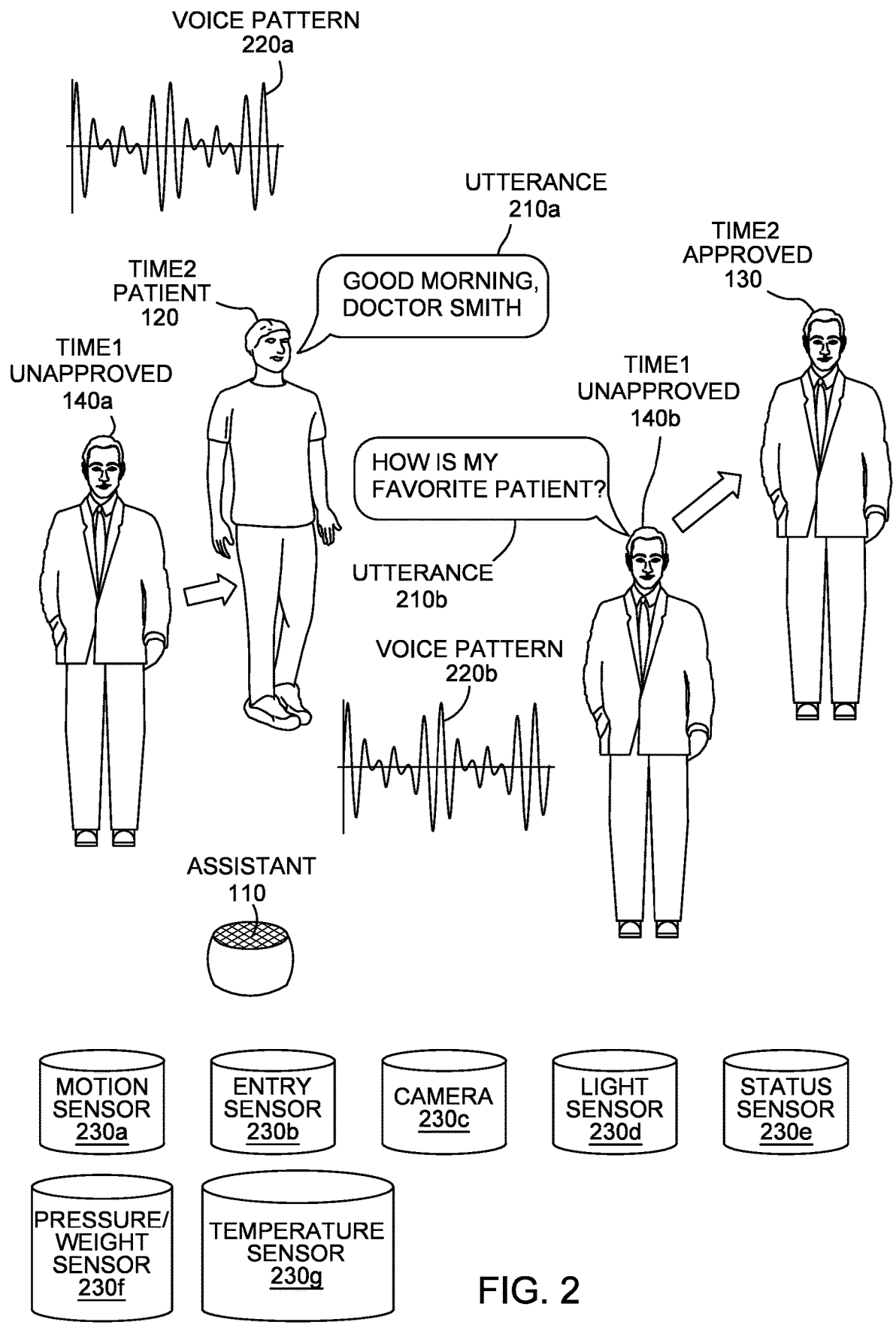
FIG. 2 illustrates a environment in which an assistant device may be deployed when identifying various parties and determining how to respond, according to embodiments of the present disclosure.

FIG. 2 illustrates a environment 200 in which an assistant device 110 may be deployed when identifying various parties and determining how to respond, according to embodiments of the present disclosure. The assistant device 110 can identify or infer the presence of a person in the environment 200 based on received audio containing speech, the sound of a door into the environment opening, or additional presence data received from sensors 230*a-g* (generally or collectively, sensors 230) in the environment, such as a motion sensor 230*a*, an entry sensor 230*b* at a doorway, cameras 230*c*, light sensors 240*d*, or the like. Other sensors 230 that may provide additional input to the assistant device 110 can include on/off status sensors 230*e* (e.g., for specific appliances or electrical circuits), pressure or weight sensors 230*f*, temperature sensors 230*g*, etc. The various sensors 230 may include or be part of a computing system 500 as described in greater detail in regards to FIG. 5.

Generally, until a person has been identified, the assistant device 110 classifies that person as an unauthorized person 140, and may ignore commands or audio from that person. For example, at Time1, the assistant device 110 may know that two persons are present in the environment 200, but may not know the identities of those persons, and therefore treats the first person as a first unauthorized person 140*a* and the second person as a second unauthorized person 140*b*.

In various embodiments, persons can identify themselves directly to the assistant device 110 or may identify other parties to the assistant device 110. For example, when a first utterance 210*a* (generally or collectively, utterance 210) is received from the first unauthorized person 140*a*, the assistant device 110 may extract a first voice pattern 220*a* (generally or collectively, voice pattern 220) from the words (including pitch, cadence, tone, and the like) to compare against other known voice patterns 220 to identify an associated known person. In the illustrated example, the first voice pattern 220*a* matches that of a patient 120, and the assistant device 110 therefore reclassifies the first unauthorized person 140*a* to be the patient 120.

The assistant device 110 may store various identity profiles for persons to identify those persons as a patient 120, authorized persons 130 for that patient, or as unauthorized persons 140 for that patient, with various levels of rights to access or provide health information for the patient 120 and various interests in collecting or maintaining data related to that person.

Once a person has been identified as a patient 120 (or other authorized party trusted to identify other persons with whom access should be granted), the assistant device 110 may rely on utterances 210 from that trusted person to identify other persons. For example, the first utterance 210*a* can be used to identify the first unauthorized person 140*a* as the patient 120 based on the associated first voice pattern 220*a*, and the contents of the first utterance 210*a* can be examined for information identifying the other party. In the illustrated example, the assistant device 110 (either locally or via remote computing resources 160) may extract the identity "Dr. Smith" from the first utterance 210*a* to identify that the second unauthorized person 140*b* is Dr. Smith, who is an authorized person 130 for the patient 120, and the assistant device 110 therefore reclassifies the second unauthorized person 140*b* to be an authorized person 130 for the patient 120.

Additionally or alternatively, the assistant device 110 may identify Dr. Smith as an authorized person 130 based on a second voice pattern 220*b* extracted from the second utterance 210*b* spoken by Dr. Smith. The voice patterns 220 may be continuously used by the assistance device 110 to re-identify Dr. Smith or the patient 120 (e.g., at a later time) within the environment 200 or to distinguish utterances 210 as coming from a specific person within the environment 200.

When multiple persons are present in the environment 200, and potentially moving about the environment, the assistant device 110 may continually reassess which person is which. If a confidence score for a given person falls below a threshold, the assistant device 110 may reclassify one or more persons as unauthorized persons 140 until identities can be reestablished. In various embodiments, the assistant device 110 may use directional microphones to establish where a given person is located in the environment 200, and may rely on the various sensors 230 to identify how many persons are located in the environment 200 and where those persons are located.

Example Sharing and Secret Keeping Scenarios

FIGS. 3A-3K illustrate example sharing and secret keeping scenarios when an assistant device 110 contends with different requestors and persons present in the environment 300, according to embodiments of the present disclosure. Although several of the example scenarios are discussed in relation to the patient 120, the assistant device 110 may also similarly interact with one or more authorized persons 130 in addition to or instead of the patient 120 in each such scenario.

Figure 3A:
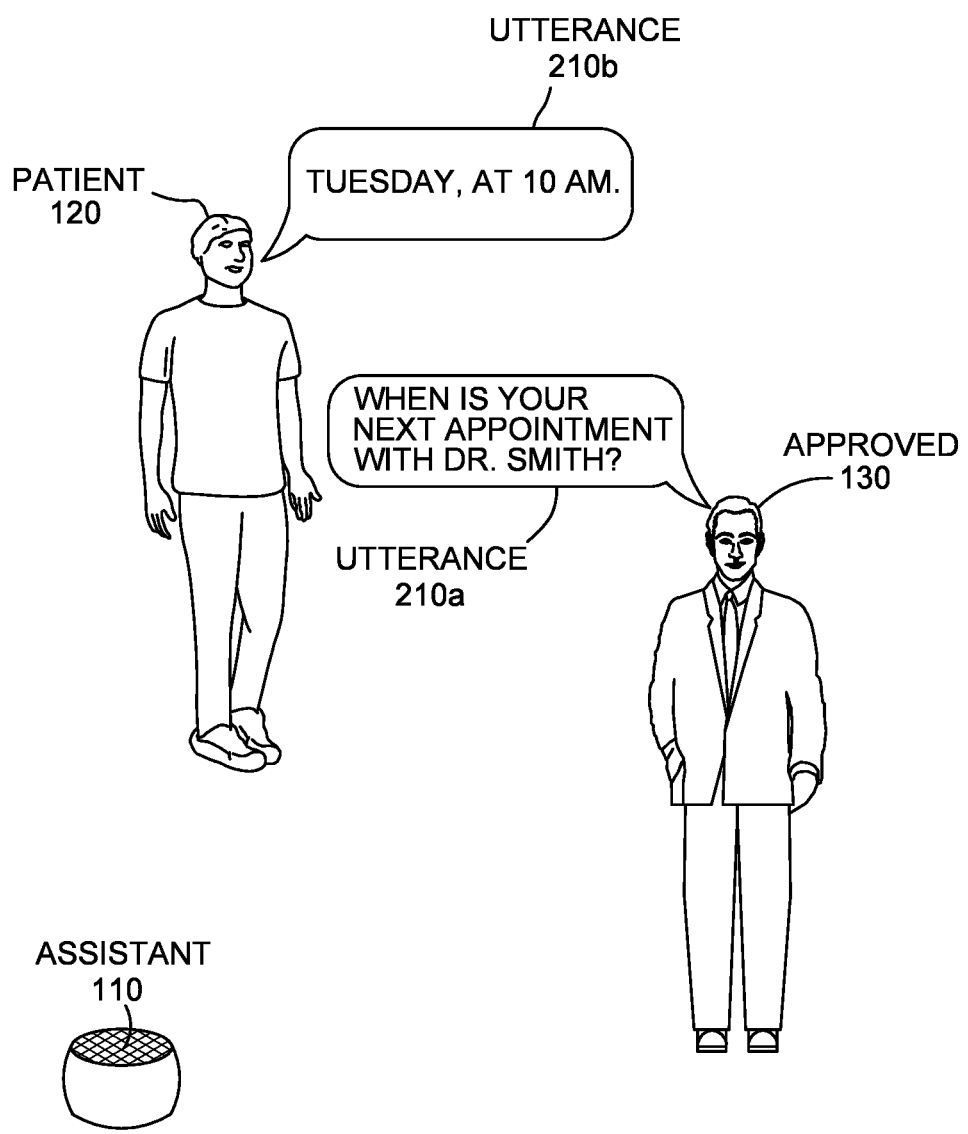
FIGS. 3A-3K illustrate example sharing and secret keeping scenarios when the assistant device contends with different requestors and persons present in the environment, according to embodiments of the present disclosure.

FIG. 3A illustrates a first scenario in which a patient 120 and an authorized person 130 are discussing health information related to the patient 120, where the patient 120 gives a complete response. As illustrated, an authorized person 130 asks a patient 120 via a first utterance 210a "when is your next appointment with Dr. Smith?", to which the patient 120 replies (accurately and fully) in a second utterance 210b "Tuesday, at 10 am". When the reply is correct (e.g., matches known data responsive to the request), the assistant device 110 can remain silent since the patient 120 answered the question and further input from the assistant device 110 would be unnecessary.

Although the first scenario shows an authorized person 130 requesting and receiving the health information from the patient 120, the patient 120 remains in control of who can and cannot be provided with the health information. Accordingly, the first scenario may be repeated with an unauthorized person 140 instead of an authorized person 130 with similar results; the patient 120 is free to share the health information, and the assistant device 110 may remain silent. However, the assistant device 110 may also react as is described in the eleventh scenario discussed in relation to FIG. 3K to alert a third party when the patient 120 decides to share certain health information to previously unauthorized persons 140.

In various embodiments, the data that the assistant device 110 checks against the request for relevance and the reply for accuracy may be cached locally on the assistant device 110 or may be stored remotely (e.g., on a cloud based calendar service, at Dr. Smith's office, etc.). Similarly, the assistant device 110 may perform some or all of the elements of speech recognition and natural language processing to determine the contents and intents of the utterances 210 locally or remotely via remote computing resources 160. However, to avoid sharing health data with a remote computing resource 160 (or confirming that such data are actually health data or accurate), the assistant device 110 may confine the comparison of the requests and replies against the known health data to localized comparisons on the assistant device 110 or localized server for a set of assistant devices 110.

Figure 3B:
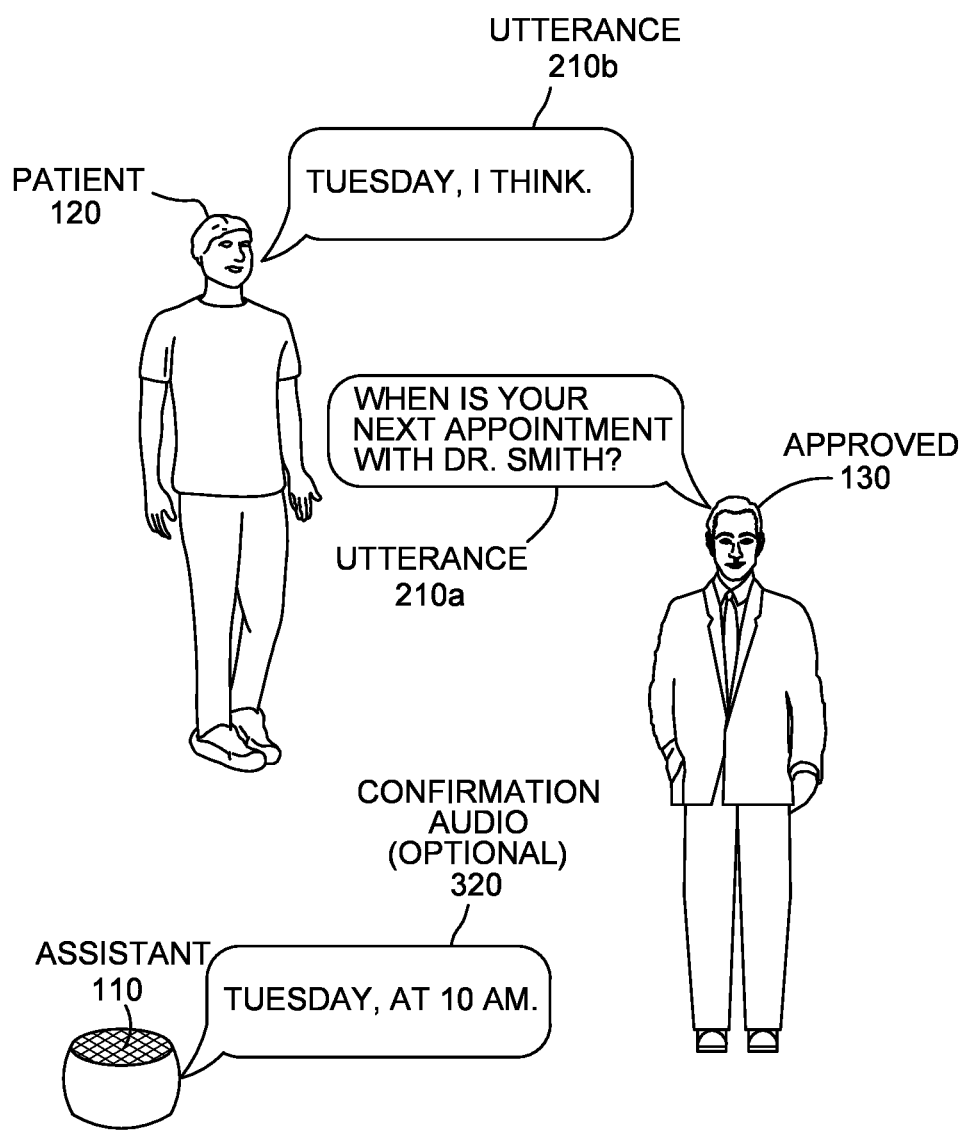

FIG. 3B illustrates a second scenario in which a patient 120 and an authorized person 130 are discussing health information related to the patient 120, where the patient 120 does not give a complete response. As illustrated, an authorized person 130 asks a patient 120 via a first utterance 210a "when is your next appointment with Dr. Smith?", to which the patient 120 replies (accurately, but with a qualifier) in a second utterance 210b "Tuesday, I think". When the reply is inaccurate (e.g., does not match known data responsive to the request), includes qualifiers (e.g., "I think"), or alternatives (e.g., "either Tuesday or Wednesday") that renders the reply not fully responsive, the assistant device 110 can interject confirmation audio 320 into the conversation to provide correct and reliable health information as part of the conversation flow. As illustrated, the assistant device 110 generates an audio output of "Tuesday at 10 am" for the confirmation audio 320 to the requestor's initial query in the first utterance 210a.

Figure 3C:
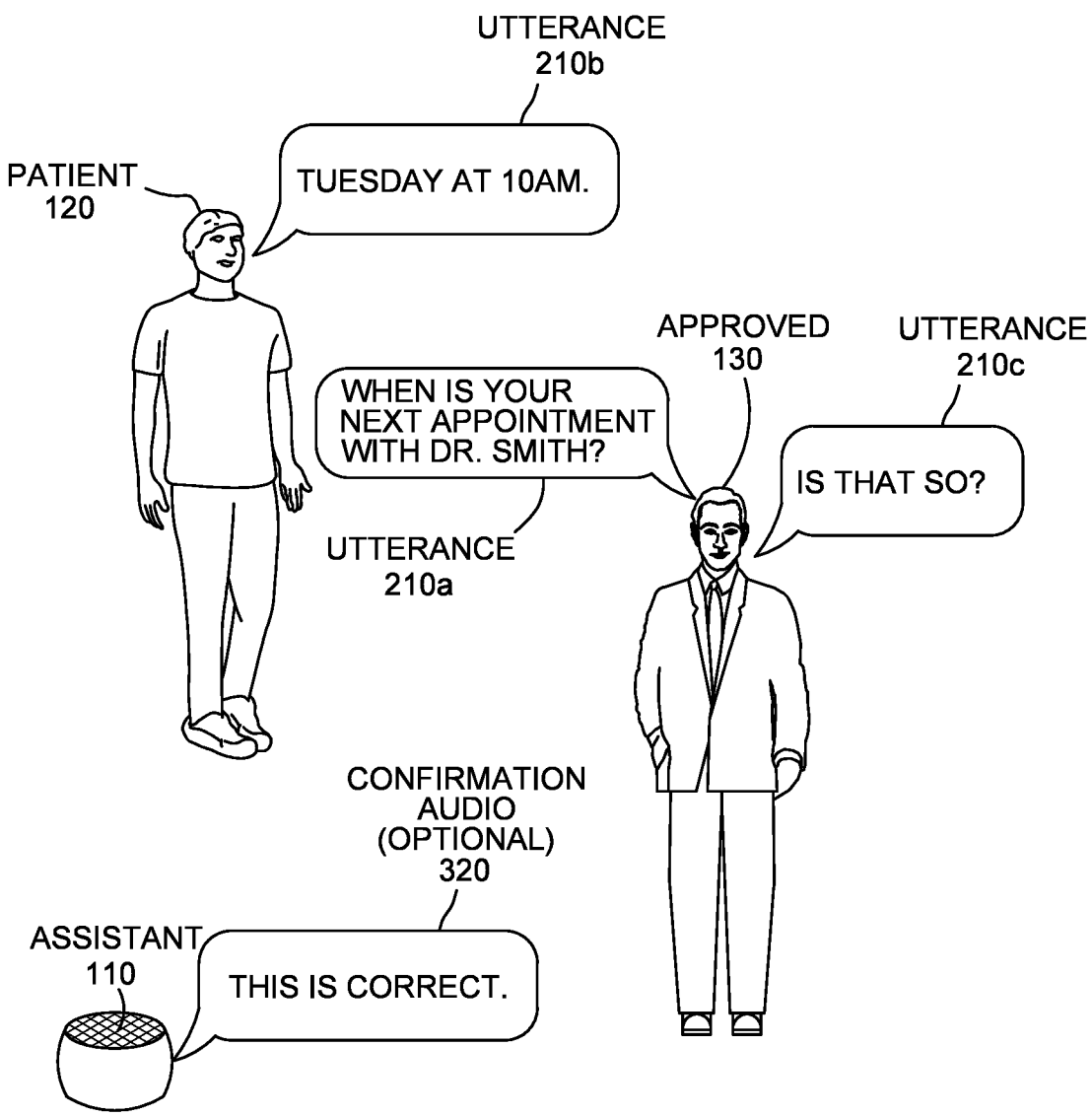

FIG. 3C illustrates a third scenario in which a patient 120 and an authorized person 130 are discussing health information related to the patient 120, where the patient 120 gives a complete response, and the authorized person 130 requests confirmation. In various embodiments, the assistant device 110 may be used in healthcare locations where the patients 120 may have unreliable memories, or the patient 120 may otherwise not be trusted to provide correct information. As illustrated, an authorized person 130 asks a patient 120 via a first utterance 210a "when is your next appointment with Dr. Smith?", to which the patient 120 replies (accurately and fully) in a second utterance 210b "Tuesday, at 10 am". However, the authorized person 130 responds to the second utterance 210b with a third utterance 210c of "is that so?" that has an intent that questions the accuracy or completeness of the reply given by the patient 120, which the assistant device 110 identifies as conversational trigger to supply confirmation audio 320 of "this is correct".

In various embodiments, when the assistant device 110 identifies the intent of an utterance 210 to be questioning the veracity or completeness of a previous utterance 210, the assistant device 110 may generate an audio output that confirms (or counters) what was previously said. For example, the assistant device 110 may supply an indication of whether what was previously said was correct or incorrect, or may supply a full response as though the initial request was not answered (e.g., "the appointment with Dr. Smith is at 10 am on Tuesday" rather than "this is correct") to supply any intentionally or unintentionally omitted information. Intent analysis may be performed locally by the assistant device 110 or remotely by various remote computing resources.

Figure 3D:
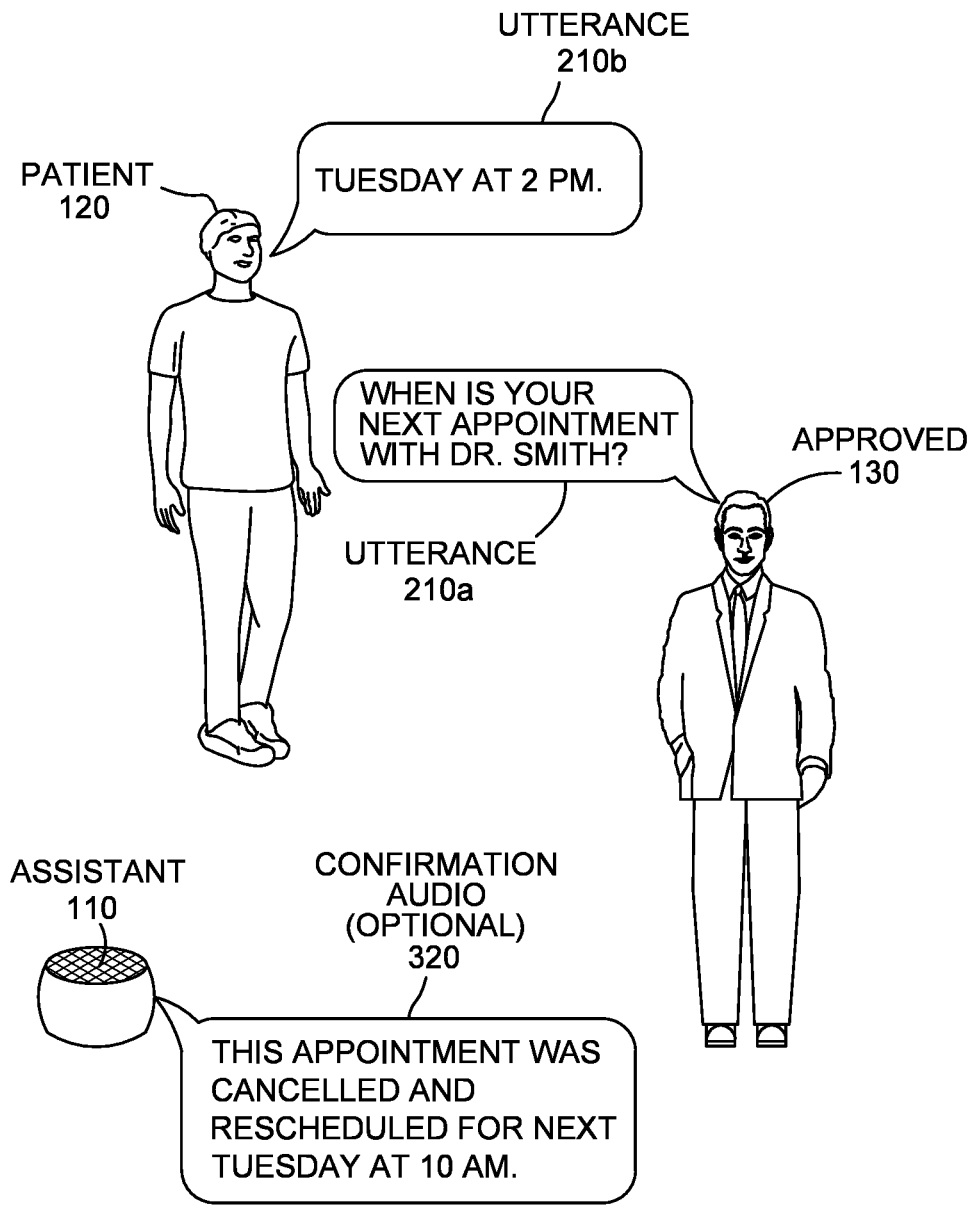

FIG. 3D illustrates a fourth scenario in which a patient 120 and an authorized person 130 are discussing health information related to the patient 120, where the patient 120 gives a false response. In various embodiments, the false response may be intentional or unintentional, but the assistant device 110 can interject into the conversation correct information to various authorized persons 130. As illustrated, an authorized person 130 asks a patient 120 via a first utterance 210a "when is your next appointment with Dr. Smith?", to which the patient 120 replies (falsely) in a second utterance 210b, "Thursday, at 2 pm". The assistant device 110 then responds to this falsehood in the second utterance 210b with confirmation audio 320 of "the appointment was cancelled and rescheduled for next Tuesday at 10 am".

In various embodiments, the assistant device 110 may recognize when the falsehood, if acted on, would lead to harm for the patient 120, and may act in an emergency capacity to mitigate or avoid harm. When prophylactically acting on the patient's behalf, the assistant device 110 may (temporarily) authorize persons in the environment 300 to receive health information to avoid harm to the patient 120. For example, when a person asks the patient 120, "do you want me to get your heart medication for you?", and the patient 120 replies "yes" when the patient 120 is no longer prescribed the given heart medication (and taking such medication would interfere with other medications or otherwise negatively affect the patient 120), the assistant device 110 may generate confirmation audio 320 of "the heart medication is no longer prescribed". As will be appreciated, other prophylactic responses to falsehoods supplied by the patient 120 may be provided in other situations where relying on the response given by the patient 120 could lead to harm.

In various embodiments, a medical professional (or a person with medical authority for the patient 120) may identify a subset of one or more medications or activities that, if responses related to that medication or activity include falsehoods, the assistant device 110 is permitted to provide a prophylactic confirmation audio 320 to address, regardless of presence of unauthorized persons 140 in the environment 300. Accordingly, falsehoods related to negative allergens (e.g., "I am not allergic to that" when the patient 120 is) or certain classes of medication and statuses thereof (e.g., "I already took medication X" or "I do not need to take medication X any more") may result in a prophylactic confirmation audio 320 that corrects the falsehood to avoid a medical harm to the patient 120 if the falsehood were acted upon. In contrast, falsehoods related to positive allergens (e.g., "I am allergic to that" when the patient 120 is not), certain different classes of medications and status thereof may not result in a prophylactic confirmation audio 320.

When correcting the falsehood, the assistant device 110 generates a confirmation audio 320 regardless of whether an unauthorized person 140 is in the environment 300, but may structure the contents of the message to avoid providing more health information than is needed to avoid the medical harm. For example, the assistant device 110 may output "please confirm all allergen details," or "that is not correct," rather than listing out loud the patient's allergies or medications.

Figure 3E:
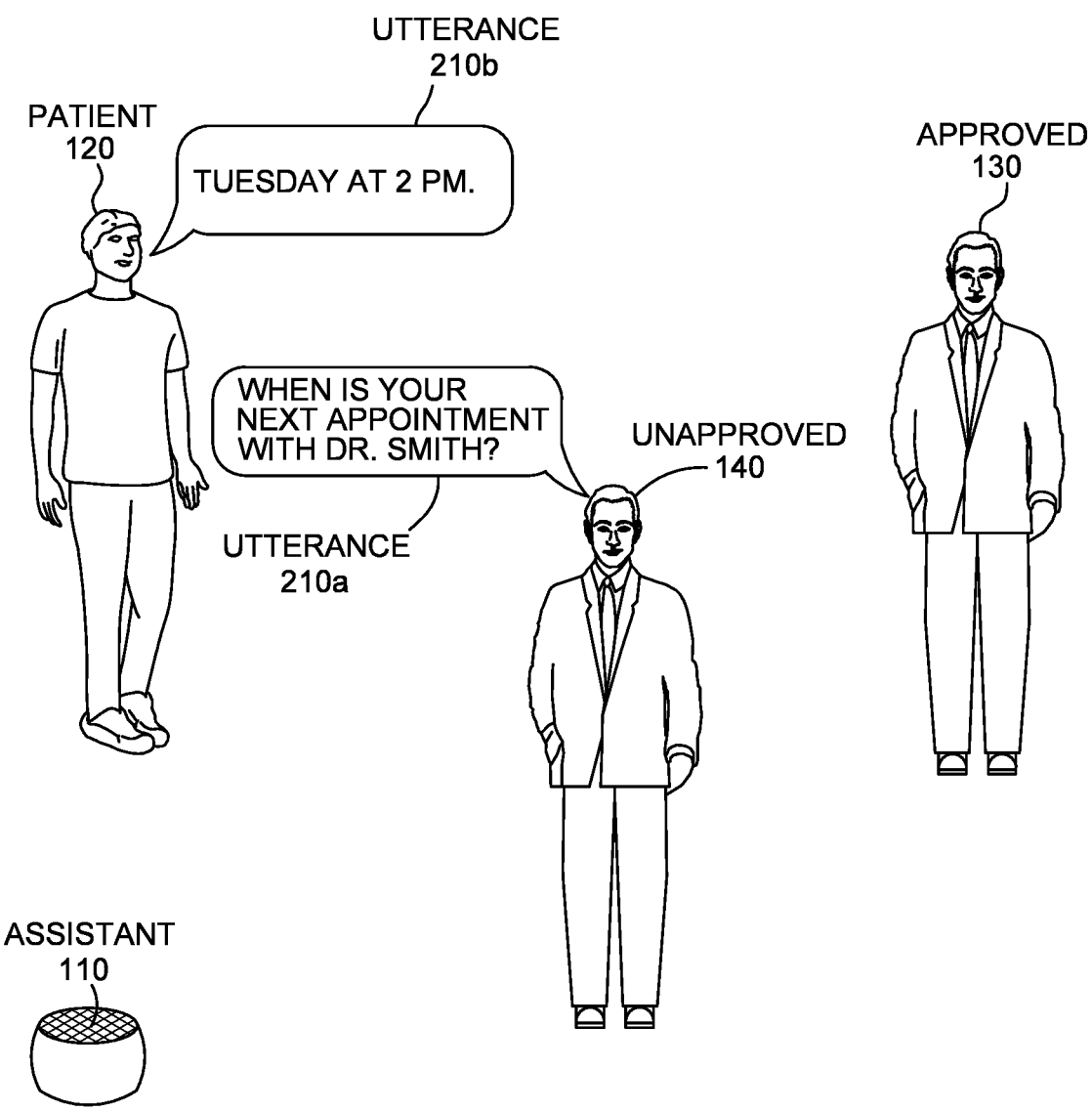

FIG. 3E illustrates a fifth scenario in which a patient 120 and an unauthorized person 140 are discussing health information related to the patient 120 in the presence of an authorized person 130. As illustrated, an unauthorized person 140 asks a patient 120 via a first utterance 210a "when is your next appointment with Dr. Smith?", to which the patient 120 replies (falsely) in a second utterance 210b, "Thursday, at 2 pm". Although the patient 120 has provided a reply that nominally satisfies the request, the contents of the reply are false, which may be due to mistake on the part of the patient 120 (e.g., misremembering the correct answer) or part of a ploy to satisfy the request without giving real information (e.g., to stop follow up questions by satisfying the requestor with a lie). Accordingly, the assistant device 110 may not know whether the patient 120 has attempted to authorize the sharing of the health information, and remains silent; not providing an audio output to correct the false statement.

The presence of the authorized person 130 does not affect the analysis of whether the assistant device 110 is permitted to share the health information in the fifth scenario. Stated differently, the status of the unauthorized person 140 being in the environment 300 prevents the assistant device 110 from sharing health information, whether in response to a request or to correct a falsehood given in a reply, unless a prophylactic response is triggered.

Figure 3F:
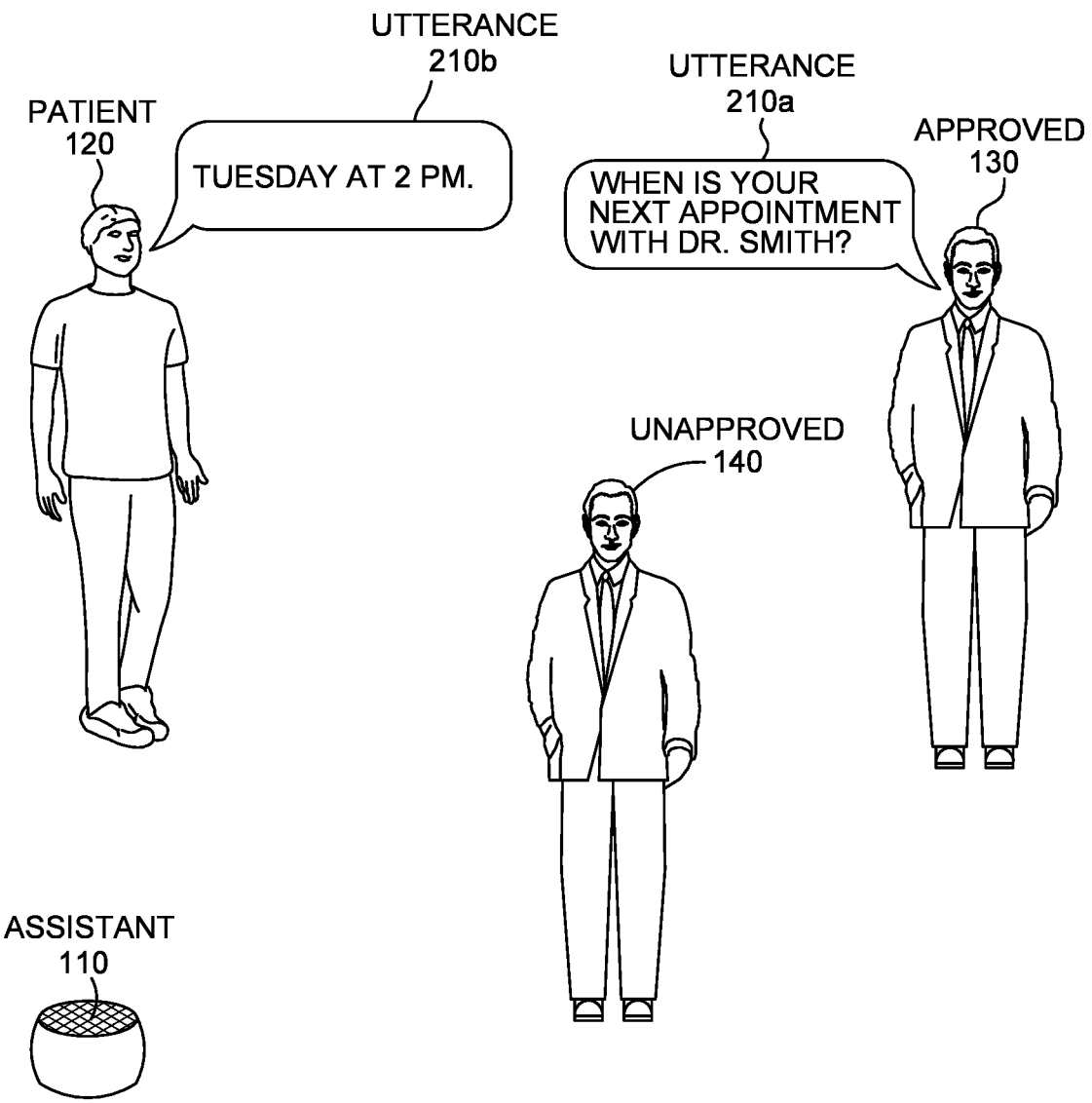

FIG. 3F illustrates a sixth scenario in which a patient 120 and an authorized person 130 are discussing health information related to the patient 120 in the presence of an unauthorized person 140. As illustrated, an authorized person 130 asks a patient 120 via a first utterance 210a "when is your next appointment with Dr. Smith?", to which the patient 120 replies (falsely) in a second utterance 210b, "Thursday, at 2 pm". Similarly to the fifth scenario shown in FIG. 3E, despite the patient 120 giving false information, the assistant device 110 may remain silent to avoid sharing health information that the patient 120 has not authorized to share with the unauthorized person 140, despite the request coming from an authorized person 130.

Figure 3G:
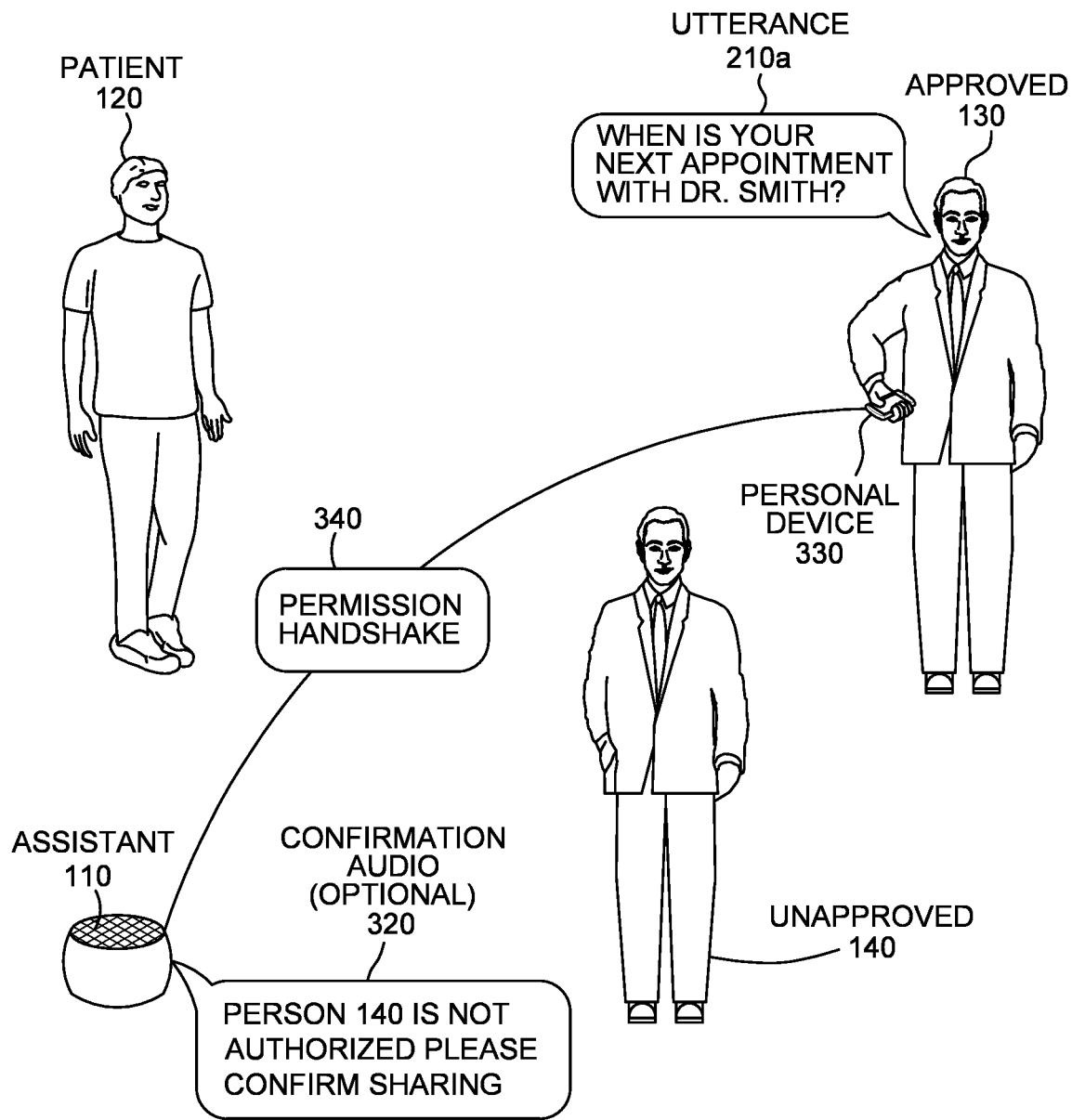

FIG. 3G illustrates a seventh scenario in which an assistant device 110 interacts with an authorized person 130 via an alternative channel from audio output when an unauthorized person 140 is present. As illustrated, an authorized person 130 asks a patient 120 via a first utterance 210a "when is your next appointment with Dr. Smith?", to which no reply is received (yet). In various embodiments, before determining whether to interject information into the conversation, the assistant device 110 determines whether to provide the information via the alternative channel privately to one or more authorized persons 130 rather than publically when an unauthorized person 140 is in the environment 100. Additionally or alternatively, the assistant device 110 may query a patient 120 or authorized person 130 via a personal device 330 to authorize a currently unauthorized person 140 to receive the health information via an audio output.

Accordingly, the assistant device 110 may interface with one or more personal device 330 (e.g., cell phones, smart watches, tablets, etc.) associated with the patient 120 or an authorized party for use as an alternative channel to privately provide the health information, or privately request authorization to share with an unauthorized person 140. In various embodiments, the assistant device 110 may perform an authorization handshake 340 with a prospective personal device 330 for use as an alternative channel to ensure that the personal device 330 is under the control of an authorized person 130 and will not act as a public conduit of health information (e.g., ensuring a text to speech application does not read aloud any communication sent to the personal device 330 from the assistant device 110). In various embodiments, the authorization handshake 340 may request a shared secret from the authorized person (e.g., a password), use facial recognition, etc., to ensure that the personal device 330 is under the control of an authorized person 130 before using the personal device 330 as an alternative channel.

Figure 3H:
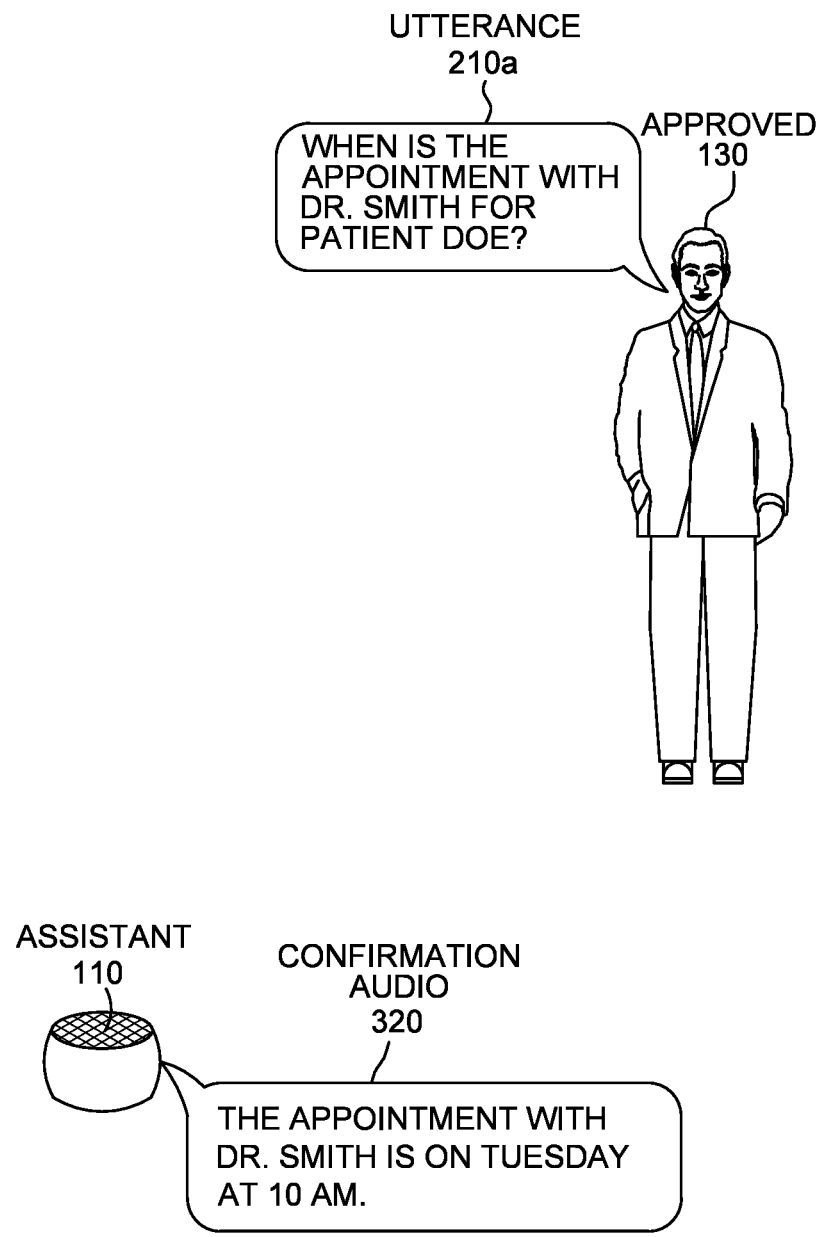

FIG. 3H illustrates an eighth scenario in which an authorized person 130 interacts with the assistant device 110 to receive health information regarding a patient 120 who is non-responsive or not present in the environment 300. As illustrated, an authorized person 130 asks the assistant device 110 "When is the appointment with Dr. Smith for Patient Doe?". After the assistant device 110 identifies that the requestor is authorized to receive the health information, and that no unauthorized persons 140 are presented in the environment 300, the assistant device 110 provides an audio output with the health information to the authorized person 130 via the confirmation audio 320 of "The appointment with Dr. Smith is on Tuesday at 10 am," even when the patient 120 is not present or otherwise non-responsive.

In various embodiments, the assistant device 110 can determine that the request is directed to the assistant device 110 (rather than a person) based on the number of persons in the environment 300 (e.g., when the requestor is the sole person), a lack of response from any persons after a threshold period after a request is posed, or the structure or intent of the utterance for the request. In some embodiments, the inclusion of a trigger phrase or activation cue for the assistant device 110, an override code (e.g., for Emergency Personnel), or a name of one or more persons in the environment 300 may serve to identify via natural language structures whether the request is directed to the assistant device 110. For example, a doctor, firefighter, or ambulance doctor may use an override code to interact with the assistant device 110 with temporarily higher rights to health information to treat an ongoing or emergent condition when the patient 120 is incapacitated or otherwise unable to provide the information (or authorization for the information) in a timely manner to avoid or mitigate harm to the patient 120 due to that condition that providing the health information help mitigate. For example, an assistant device 110 may provide health information for the location of epinephrine for a patient 120 who is undergoing anaphylactic shock to persons who identify themselves as emergency responders.

Figure 3I:
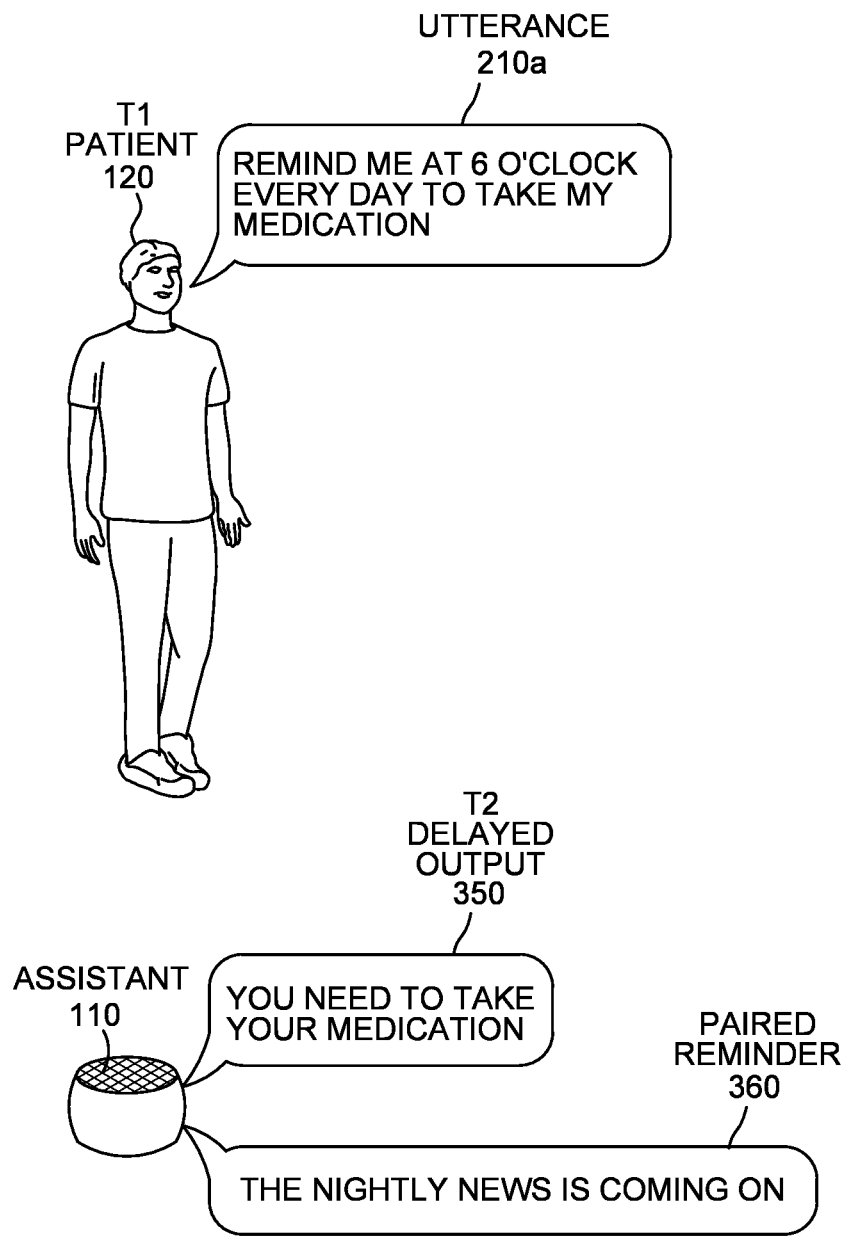

FIG. 3I illustrates a ninth scenario in which a delayed provision of health information is set up for the assistant device 110. As illustrated, a patient 120 asks the assistant device 110 via a first utterance 210a at time T1 to "remind me at six o'clock every day to take my medication" which the assistant device 110 uses to schedule the delayed or triggered provision of health information, for example, for medication or appointment reminders. Once the conditions for the delayed or triggered provision of health information are satisfied, at a later time T2, the assistant device 110 provides an audio output of a delayed output 350 of "take your medication" to the patient 120. In various embodiments, when supplying a delayed output 350, the assistant device 110 monitors the environment at time T2 to determine that no unauthorized persons 140 are present before supplying the health information via an audio output as is described in the other scenarios.

In various embodiments, the assistant device 110 may ensure that the requestor (or a party designated by the requestor) is present as a condition to provide the delayed output 350 (e.g., to prevent broadcasting health information to an empty environment or an uninterested, but authorized, person). Additionally, because the party for whom the delayed output 350 is requested may not run on time, any time-based trigger may include fuzzy matching for the time in question rather that strict time matching so the persons for whom the delayed output 350 is intended actually receive the health information when they are present with the assistant device 110 within a threshold time of the originally set trigger time (e.g., T2±5 minutes).

In addition to or instead of time-based triggers, (e.g., "at six o'clock", "in twenty minutes", etc.) the assistant device 110 may set recurring delayed times, event-driven triggers (e.g., "when I get back from the store," "when I wake up", etc.), and combinations thereof. Additionally, the assistant device 110 can pair health-related triggers with non-health information that are triggered off of the same time, event, or recurring schedule as the health information delayed outputs 350. For example, in addition to reminding the patient to take medication every day at six pm, the assistant device 110 can also provide a reminder to "call your parents" or "the nightly news is coming on" at or around six pm every day to build a Pavlovian response into the patient 120 linked to the non-health information. In this way, the patient 120 can associate calling their parents or watching the nightly news with taking their medication and receive only the paired reminder 360 when unauthorized persons 140 are present, but still feel the need or automatically trigger a memory to also take their medication.

Figure 3J:
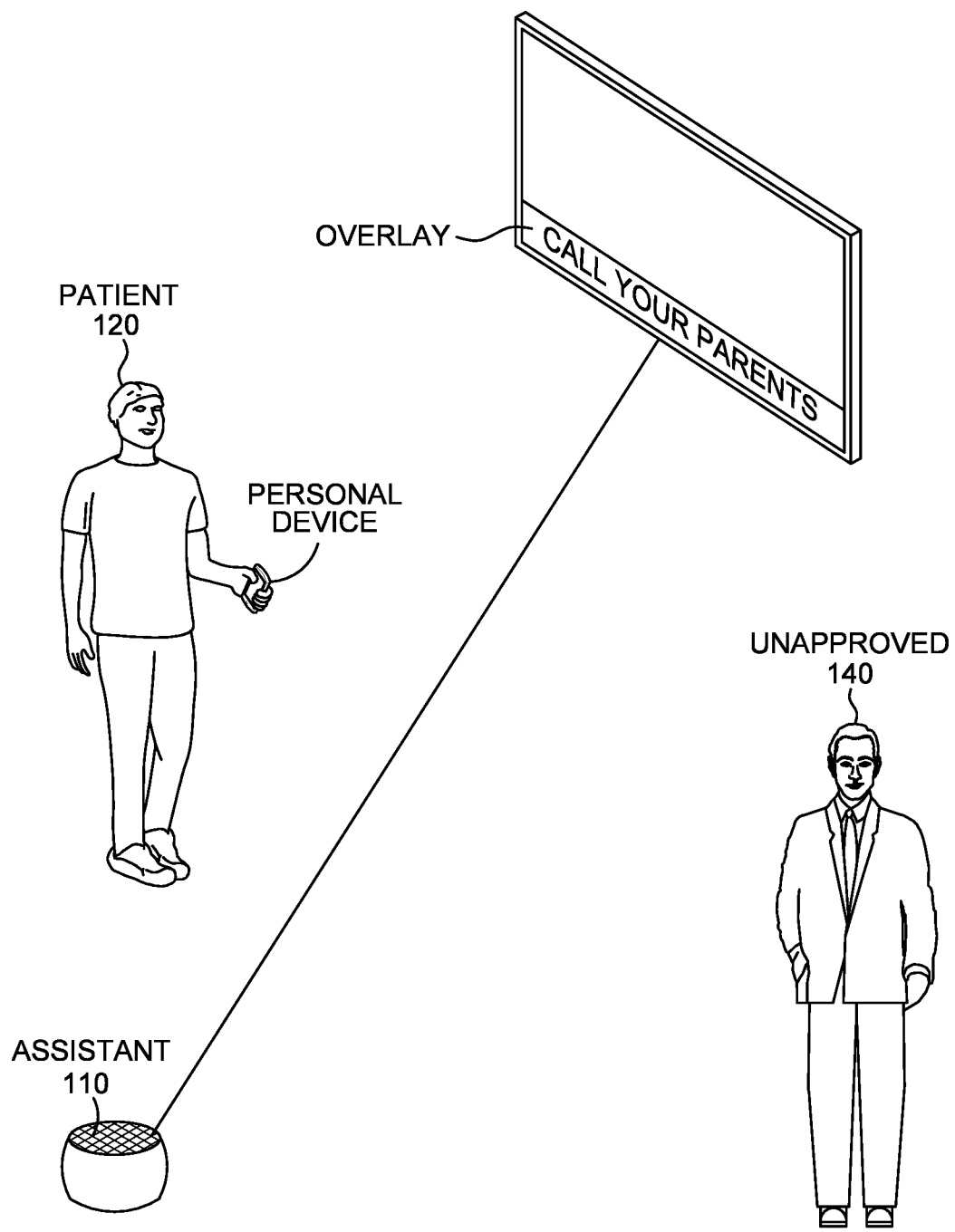

FIG. 3J illustrates a tenth scenario in which the assistant device 110 uses alternative channels to interact with a patient 120 regarding health information. For example, rather than providing the paired reminder 360 via an audio output, the assistant device 110 may interface with a personal device 330 or a video device 370 (e.g., a television), to provide the contents of the paired reminder 360 via images (e.g., via an overlay 380 over a program displayed on the video device 370). In various embodiments, the assistant device 110 may provide the non-health related paired reminder 360 publically or without verifying possession of a personal device 330 as the health-related subtext of the paired reminder 360 is hidden from the unauthorized persons 140 in the environment.

Figure 3K:
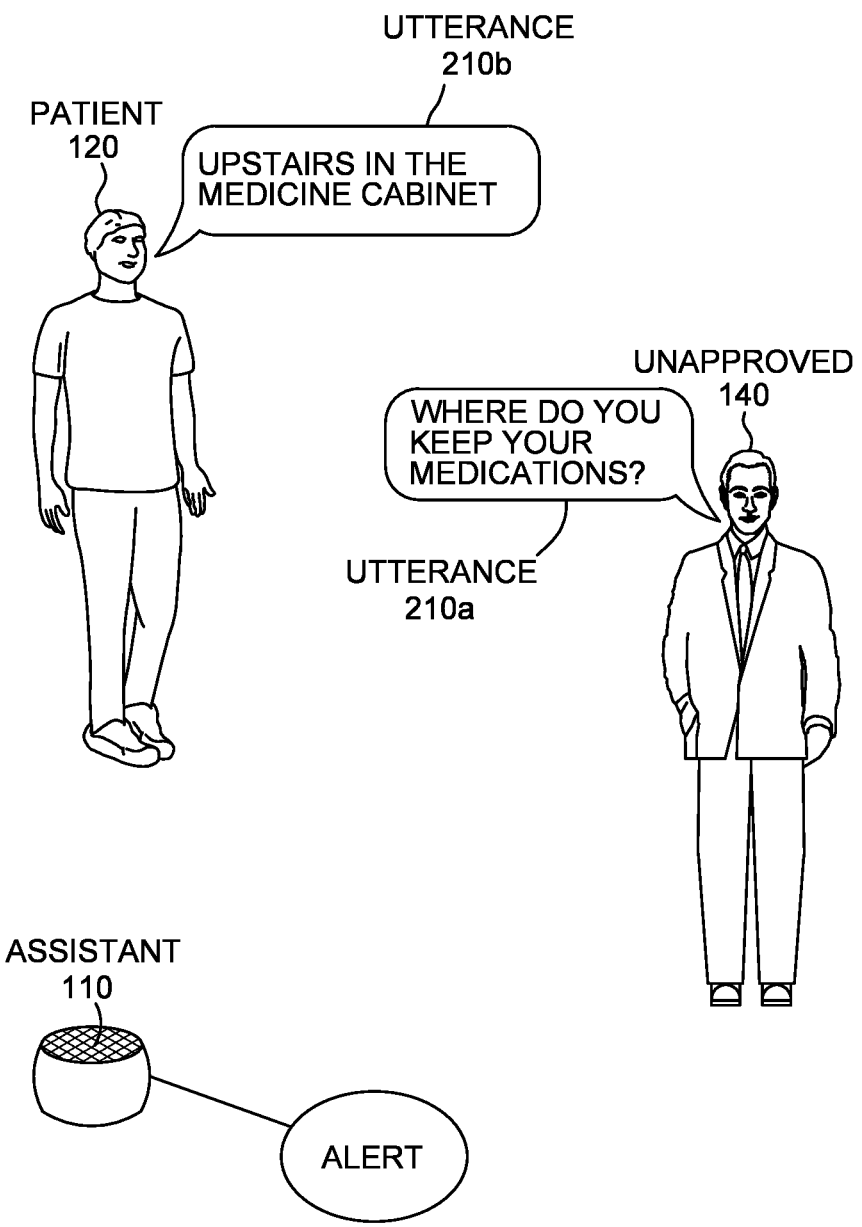

FIG. 3K illustrates an eleventh scenario in which the assistant device 110 sends an alert 390 to a trusted party when an unauthorized person 140 asks for certain health information. In various embodiments, the trusted party may set an email address, a personal device 330, or other service to receive the alert 390 via various communications pathways (e.g., automated phone call, email, text message, in-application message, etc.) As illustrated, an unauthorized person 140 asks a patient 120 in a first utterance "where do you keep your medications", which may be designated as dealing not only with restricted health information, but health information of particular concern. Accordingly, although the patient 120 replies "upstairs in the medicine cabinet", which may indicate that the patient 120 is authorizing the (initially) unauthorized person 140 to know where the medication is located, the assistant device 110 generates an alert 390 when such information is requested.

Accordingly, the third party can evaluate whether the request is of concern (e.g., someone attempting to steal medication) and should be acted on, or not of concern. When generating the alert 390, the assistant device 110 may remain silent.

Example Methodologies

Figure 4:
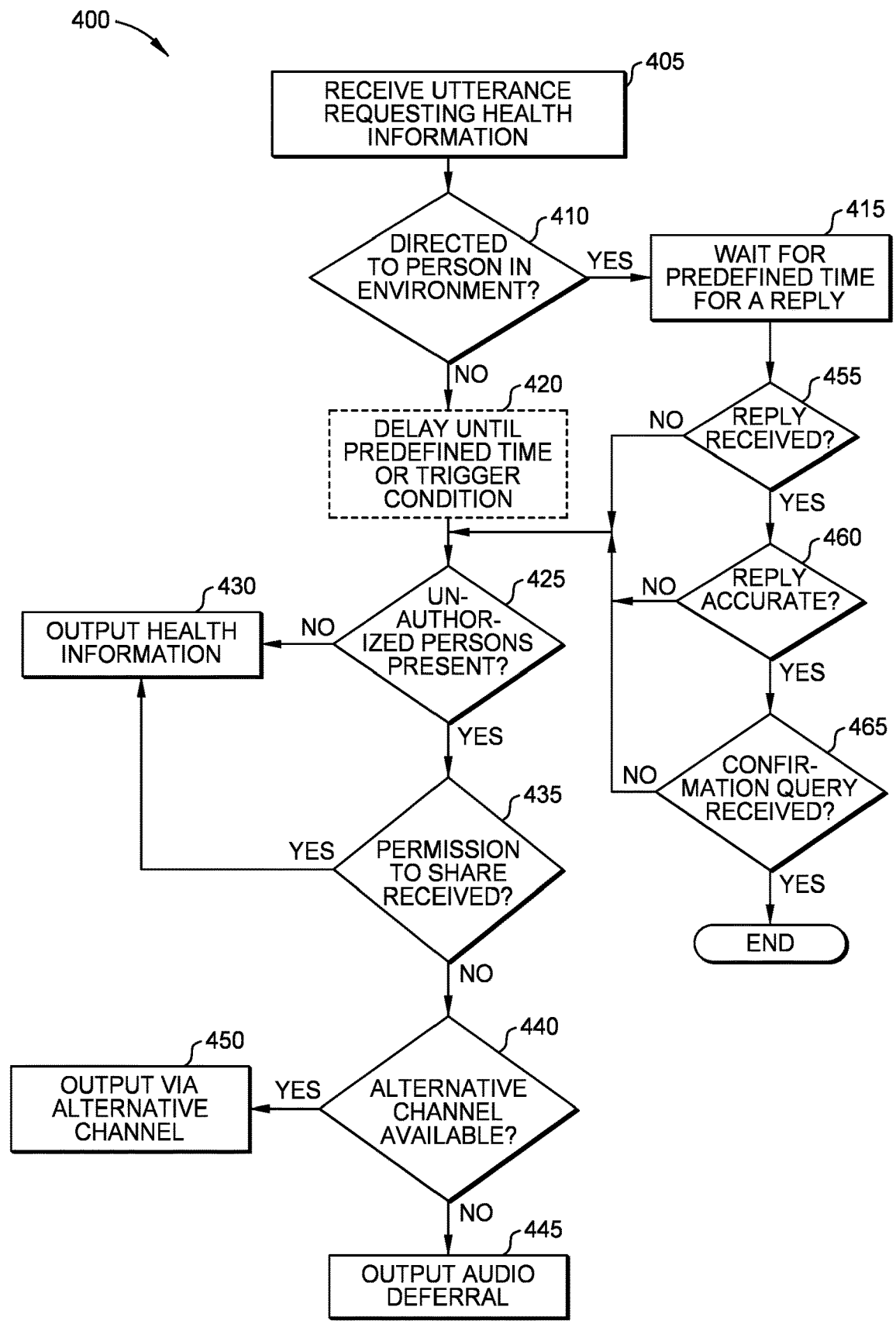
FIG. 4 is a flowchart of a method for determining when to share restricted health information via an assistant device, according to embodiments of the present disclosure.

FIG. 4 is a flowchart of a method 400 for determining when to share restricted health information via an assistant device, according to embodiments of the present disclosure. Method 400 begins at block 405, where the assistant device receives an utterance requesting health information from a requestor in the environment. In various embodiments, the utterance can be directed to a patient (or other knowledgeable party) or the assistant device, may include a request for immediate response or delayed response (e.g., a request to provide the health information at a later time as a reminder), and the information may be requested in the presence of persons who are not authorized to receive the health information from the assistant device. Accordingly, method 400 includes several checks to allow the assistant device to quickly and accurately supply the requested health information when doing so would not compromise data security. Although the blocks indicated in method 400 may be performed in various other orders from what is illustrated, the order of operations in method 400 indicate an effective mode of analysis for whether and how to provide requested health information, which provides for faster computation of the determination (e.g., conserving computing resources by avoiding unnecessary computations) and more accurate results than other modes or previous methods.

At block 410, the assistant device determines whether the request is directed to a person in the environment or to the assistant device. In various embodiments, the assistant device determines the target of the request based on the presence of a cue command to invoke the assistant device (e.g., the request beginning with the name of the AI assistant) or a personal name of a person in the environment. In various embodiments, when the utterance does not include a cue command, the assistant device determines that the request is directed to a person in the environment. For example, a conversation may variously include or omit the names of the participants (particularly after the parties are introduced), and the assistant device therefore may refrain from interjecting information into the conversation unless specifically invoked or in response to one of the participants supplying incorrect information or otherwise not providing a response.

If the request is directed to the assistant device, method 400 proceeds to block 420 where the assistant device optionally waits until a predefined time or for a trigger condition before proceeding to block 425. In various embodiments, the request may be a request for immediate provision of health information, for example, part of a conversation between various parties that the assistant device interjects into, or a request for a future interjection. For example, a requestor (who may be the patient) may request the assistant device to provide a reminder at some time (or some repeating time) in the future, such as, for example, a reminder to take medication at a certain time every day. In another example, a requestor may request that the assistant device output a reminder after a visitor leaves (e.g., "remind me to call Dr. Smith after my neighbor leaves") or other triggering event.

At block 425, the assistant device determines whether one or more unauthorized persons are present in the environment. In various embodiments, the assistant device is in communication with one or more sensors in the environment, which can include motion sensors, cameras, or entry sensors to determine a number of persons in the environment, and optionally assign identities to those persons (e.g., based on facial recognition). The assistant device may also identify the various persons based on voice recognition or interpersonal identification via speech recognition (e.g., an utterance supplying a person's name).

When one or more unauthorized persons are identified in the environment, which may include persons identified in the environment but not yet identified as being the patient or an authorized person, method 400 proceeds to block 435. Otherwise, when all of the persons in the environment have been identified as the patient or as authorized persons, method 400 proceeds to block 430.

At block 430, the assistant device outputs the health information via an audio response. For example, when the request asks "when is the next appointment with Dr. Smith?" the assistant device may synthesize an audio response to output the answer of "Tuesday at 10 am" to the environment and any persons therein via one or more speakers. Similarly, when the request is for a delayed response of "remind me to take my medications at six pm", the assistant device delays (per block 420) until six pm, and determines at that time (per block 425) whether any unauthorized persons are present before synthesizing an audio response of "it is six pm, please take your medications". In various embodiments, the synthesized audio response may use a computer generated "voice" associated with the assistant device, or a voice associated with a trusted third party of the patient (e.g., the voice of a doctor or a family member) that the patient may be more likely to listen to and follow directions from.

In various embodiments, the assistant device may, in addition or instead of using an audio output, make use of one or more alternative channels to provide the health information. For example, a patient may infrequently wear hearing aids, and the assistant device may supplement the audio response with a message sent to a cell phone (e.g., alerting via a vibrate function) as a text message (e.g., via Short Message Service (SMS) or Multimedia Messaging Service (MMS) messages) or an application-specific message. In another example, the assistant device may interface with a television to provide an overlay over a currently displayed program to provide the health information to authorized parties in the environment.

If an unauthorized person is present, the method instead proceeds to block 435 where the assistant device determines whether permission to share with the (currently) unauthorized persons has been received. In various embodiments, the assistant device may attempt to identify any currently unidentified persons in the environment or request an authorized person to confirm authorization for the information to be shared (e.g., at least temporarily authoring the persons present to receive the health information). In various embodiments, the assistant device may generate an audio warning or request for authorization (e.g., "you are not authorized to receive health information, please identify or ask for permission").

Additionally or alternatively, the assistant device may send a non-audio warning or request to a paired device (e.g., the cellphone of a patient or authorized party) to grant authorization to share the health information. In some embodiments, the authorization may be sent to a paired device in the environment (e.g., via a WiFi® or Bluetooth® connection) or to a remote device (e.g., via a public network, such as the Internet or cell communication network). For example, a trusted party of the patient may receive alerts when the patient (or the assistant device) is asked to provide sensitive health information to an unauthorized party, to help a remotely located trusted party identify if the patient is being taken advantage of.

If authorization is not received, the method proceeds to block 440 where the assistant device determines whether any alternative channels are available beyond announcing data via an audio output to the environment or request additional data via an audio request. For example, the assistant device may interface with a cell phone (e.g., via a text message, an automated phone call, or in-application message) to provide information in addition to or instead of the audio output.

In some embodiments, the alternative channel includes an obscurable message that does not include the health information, but may direct the requestor to an alternative source for the health information, or provide a portion of a paired reminder. For example, when the assistant device is provided in a shared space (e.g., a common room of an assisted living facility), the assistant device may inform the requestor to ask for the information in a personal room to avoid sharing the health information with other persons in a public environment (e.g., "patient Doe, please return to your room for important information"). In another example, instead of providing a routine paired reminder that a patient's favorite television program is going to be aired soon and that the patient should take a daily medication before the program airs, the assistant device may output the non-health related portion of the routine paired reminder (e.g., that a patient's favorite television program is going to be aired soon) to trigger the patient to remember via a Pavlovian response to take the appropriate medication.

When no alternative channels have been established, method 400 proceeds to block 445. Otherwise, when an alternative channel exists, method 400 proceeds to block 450.

At block 445, the assistant device outputs an audio deferral to the environment. In various embodiments, the audio deferral may be silence (e.g., the assistant device not generating an audio output in response to a query) or an active denial of requested health information. For example, the assistant device may state out loud via synthesized voice that, "I cannot share that information at this time," "at least one unauthorized party is present, please ask again later," "that request is for restricted information." Method 400 may then conclude.

At block 450, the assistant device outputs a response via an alternative channel. Depending on what alternative channels exist, the assistant device may provide a non-audio output via a television, a cell phone, a dedicated personal device (e.g., a smart watch), etc., that includes the health information in a format that is not publically shared in the environment. Additionally or alternatively, the assistant device may provide an audio output that does not include the health information, but is associated with the health information by the requestor (e.g., the non-health portion of a paired reminder). Method 400 may then conclude.

Returning to block 410, if the request is directed to a person rather than the assistant device, the method proceeds to block 415 where the assistant device waits for a predefined time to receive a reply from the person to whom the request was directed. In various embodiments, the assistant device may continue processing the utterances received while waiting to receive a reply, but does not respond during the predefined time period to allow the person to whom the request was directed (or another on that person's behalf) to have time to formulate and provide an answer. In various embodiments, as natural conversation may include various breaks and tangents, a subsequently received request or a request for clarification (e.g., "could you repeat that" or "speak up!") may act as an escape from block 415; terminating a first instance of method 400 and beginning a new instance of method 400, or may act to reset a counter for the predefined time.

At block 455, the assistant device determines whether a reply was received. If no reply has been received within the predefined time period from receiving the request, method 400 proceeds to block 425 to assume responsibility for potentially answering on behalf of the person originally addressed by the request. Otherwise, if a reply has been received to the request from another person in the environment, method 400 proceeds to block 460.

At block 460, the assistant device determines whether the reply included accurate information about the requested health information. In various embodiments, the assistant device performs speech analysis on the request to determine what health information that the request is seeking, and on the reply to determine what health information that the reply is providing. The assistant device looks up the values for the requested health information, and compares the health information provided in the reply to determine whether the two match.

For example, when the requestor requests "when is your next appointment with Dr. Smith" and the patient replies "Tuesday", the assistant device identifies the intent of the request to be to learn when the patient's next appointment is, and therefore looks up when that appointment takes place. In various embodiments, the assistant device may look up the answer in locally cached information before attempting to look up the answer in a remote computing resource (e.g., a cloud based calendar) or a remotely hosted health record (e.g., a system associated with a doctor's office).

When the information supplied in the reply matches the stored health information, the assistant device determines that the reply included accurate information. Otherwise the assistant device determines that the reply does not include accurate information. As will be appreciated, human language includes several ways to express the same content, and the assistant therefore may use a fuzzy matching algorithm to determine whether the reply includes accurate information. For example, if the request is received on Monday to learn about an appointment scheduled for Tuesday, both a reply of "Tuesday" and a reply of "tomorrow" include accurate health information as both recitations refer to the same correct concept.

Additionally, various extraneous information can be included in the reply that the assistant device considers when determining whether the intent of the reply provides accurate health information. For example, when the requestor requests "when is your next appointment with Dr. Smith" and the patient replies "Tuesday or Thursday" or "I think Tuesday, but I don't know", the inclusion of "Thursday" or "but I don't know" may render the reply non-responsive and thus prevent the reply from being classified as accurate.

If the reply includes accurate health information, method 400 proceeds to block 465. Otherwise, method 400 proceeds to block 425 to determine whether the assistant device can interject with a response that does include the correct health information for the request issued per block 405.

At block 465, the assistant device determines whether a confirmation query has been received in the environment. For example, after the health information has been accurately provided to the requestor by the other person in the environment, the requestor (or a second requestor) may wish to confirm the accuracy of the supplied health information as a follow up to the initial utterance. The confirmation query may be structured as a query to the patient or the replying party (if different than the patient), or directly to the assistant device. For example, a requestor may initially ask "when is your next appointment with Dr. Smith" (per block 405), and the patient accurately replies "next Tuesday", but the requestor may doubt the patient's memory, and may ask "are you sure that your appointment with Dr. Smith is next Tuesday?" as a confirmation query.

In various embodiments, the assistant device identifies an utterance as including a confirmation query (rather than a second request for more or different health information or a non-health related utterance) based on a speech analysis of the utterance received after the reply is received. In various embodiments, the assistant device may use various trigger words, such as, "are you sure," "really", "are you certain", etc., to identify a confirmation query from a second request. Additionally or alternatively, the assistant device may look for various repeated words or phrases between the reply and a potential confirmation query so that when an utterance repeats various portions of a reply, that utterance is considered to be a confirmation query. For example, when a patient replies "next Tuesday" and an utterance including "Tuesday?" is received, the assistant device can note the repeated element of "Tuesday" and identify the utterance as a confirmation query.

The assistant device may perform further speech analysis on an utterance suspected of being a confirmation query to ensure that the utterance is coming from a different person than the initial responder and is a question. For example the assistant device may use tone analysis to determine whether the requestor is musing aloud or repeating the response for their own benefit versus asking a question (e.g., "Tuesday" versus "Tuesday?"). In some embodiments, the assistant device may detect a question based on with a rising inflection (indicative of a question in English). In other languages, such as tonal languages, the assistant device may look to identify various participles indicative of questions (e.g., "-ma" in Cantonese or "-ne" or "-ka" in Japanese) to differentiate confirmation queries from other utterances.

If a confirmation query is received, method 400 proceeds to block 425 to determine whether (or how) the assistant device can confirm the accuracy of the reply. Unlike the general case of an utterance that may be directed to a person in the environment or the assistant device to answer, because the confirmation query calls into doubt the accuracy of the responder, the assistant device may assume that the confirmation query is directed to the assistant device and bypass block 410 and block 420 when determining whether to respond to the confirmation query.

If no confirmation query is received within a predefined time window, method 400 may conclude or restart at block 405 if the requestor asks for more or different health information in response to the reply. For example, if the confirmation query asks "what time next Tuesday," or "what medication do you need to bring to your appointment," the request for the appointment time or medication may be treated as a new request for health information, and may restart method 400.

Example Computing Hardware

Figure 5:
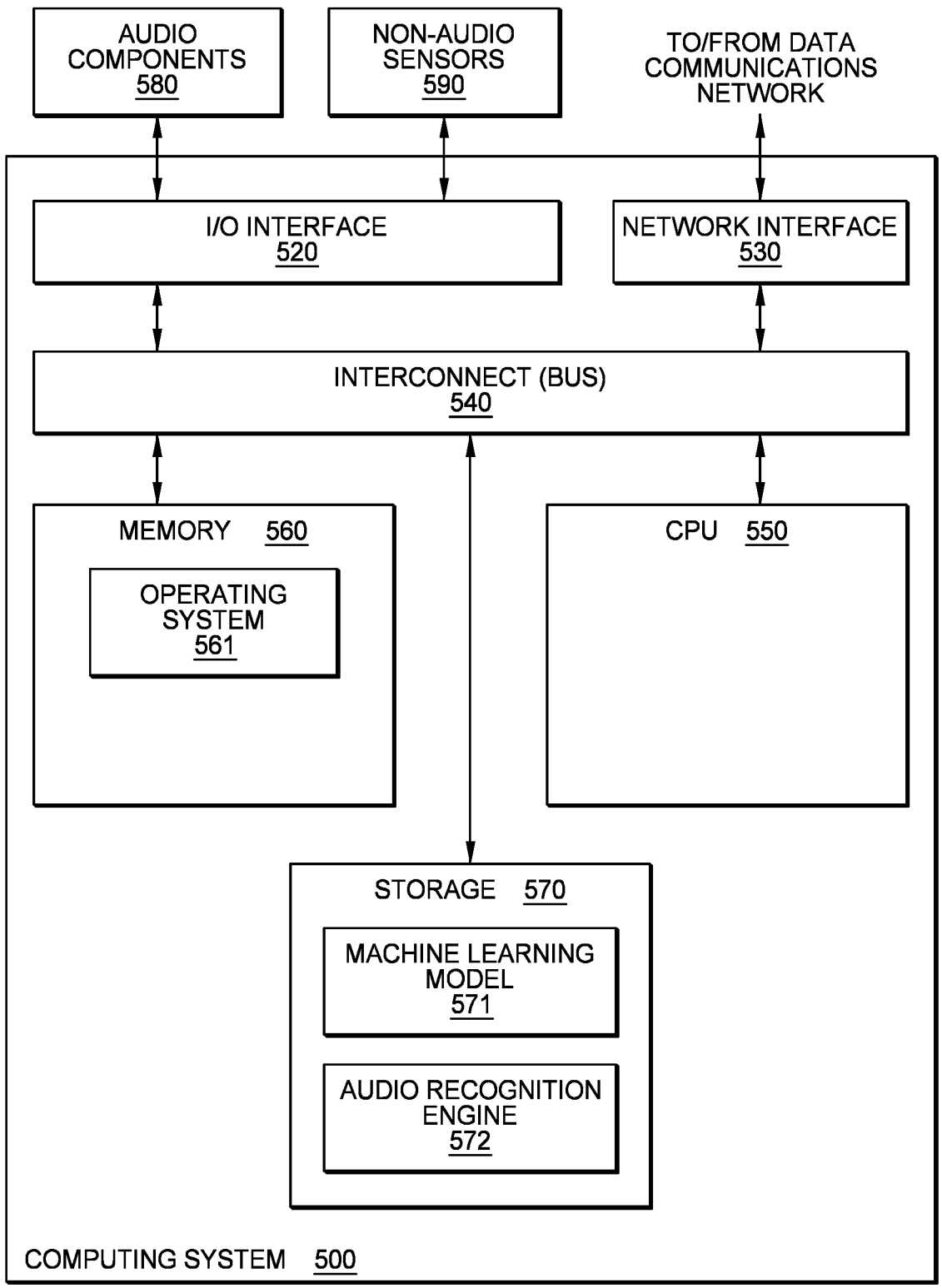
FIG. 5 illustrates a computer system, according to embodiments of the present disclosure.

FIG. 5 illustrates a computing system 500, which may be an assistant device 110, a personal device 330 (e.g., a computer, a laptop, a tablet, a smartphone, etc.), or any other computing device described in the present disclosure. As shown, the computing system 500 includes, without limitation, a central processing unit (CPU) 550, a network interface 530, an interconnect 540, a memory 560, and a storage 570. The computing system 500 may also include an I/O device interface 520 connecting I/O devices 510 (e.g., keyboard, display and mouse devices) to the computing system 500.

The CPU 550 retrieves and executes programming instructions stored in the memory 560. Similarly, the CPU 550 stores and retrieves application data residing in the memory 560. The interconnect 540 facilitates transmission, such as of programming instructions and application data, between the CPU 550, I/O device interface 520, storage 570, network interface 530, and memory 560. The CPU 550 is included to be representative of a single CPU, multiple CPUs, a single CPU having multiple processing cores, and the like. And the memory 560 is generally included to be representative of a random access memory. The storage 570 may be a disk drive storage device. Although shown as a single unit, the storage 570 may be a combination of fixed and/or removable storage devices, such as magnetic disk drives, flash drives, removable memory cards or optical storage, network attached storage (NAS), or a storage area-network (SAN). The storage 570 may include both local storage devices and remote storage devices accessible via the network interface 530. One or more machine learning models 571 may be are maintained in the storage 570 to provide localized portion of an AI assistant via the computing system 500. Additionally, one or more AR engines 572 may be maintained in the storage to match identified audio to known events occurring in an environment where the computing system 500 is located.

The AI assistant device can use a variety of different machine learning algorithms or models 571 to perform the functions described herein. The AI assistant device can use the machine learning model 571 for detecting authorized and unauthorized persons using any type of object detection algorithms (e.g., convolution neural network (CNN), fully convolutional network (FCN), or You Only Look Once (YOLO)). In one embodiment, the AI assistant device can be trained to recognize authorized persons. For example, during start up, the AI assistant device can perform a training process where the AI assistant device, using an internal camera or separate camera, captures images of an authorized person (or persons). These images can then be used to train the machine learning model 571 in a supervised learning process. That way, when capturing additional images of a person during real-time operation, the machine learning model 571 can predict whether that person is an authorized or unauthorized user.

Further, the computing system 500 is included to be representative of a physical computing system as well as virtual machine instances hosted on a set of underlying physical computing systems. Further still, although shown as a single computing system, one of ordinary skill in the art will recognize that the components of the computing system 500 shown in FIG. 5 may be distributed across multiple computing systems connected by a data communications network.

As shown, the memory 560 includes an operating system 561. The operating system 561 may facilitate receiving input from and providing output to various audio components 580 and non-audio sensors 590. In various embodiments, the audio components 580 include one or more microphones (including directional microphone arrays) to monitor the environment for various audio including human speech and non-speech sounds, and one or more speakers to provide simulated human speech to interact with persons in the environment. The non-audio sensors 590 may include sensors operated by one or more different computing systems 500, such as, for example, presence sensors, motion sensors, cameras, pressure or weight sensors, light sensors, humidity sensors, temperature sensors, and the like, which may be provided as separate devices in communication with an assistant device 110, or a managed constellation of sensors (e.g., as part of a home security system in communication with an assistant device 110). Although illustrated as external to the computing system 500, and connected via the I/O interface 520, in various embodiments, some or all of the audio components 580 and non-audio sensors 590 may be connected to the computing system 500 via the network interface 530, or incorporated in the computing system 500 and directly connected to the interconnect 540.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

The following clauses describe various embodiments of the present disclosure.

Clause 1: A method comprising receiving, at an Artificial Intelligence (AI) assistant device from a requestor in an environment, an utterance including a request to provide health information related to a patient, confirming, via a machine learning model hosted by the AI assistant device, whether an unauthorized person is present in the environment with the AI assistant device, wherein the unauthorized person is not permitted by the patient to receive the health information but is permitted to interact with the AI assistant device; and in response to determining that the unauthorized person is present, generating, by the AI assistant device, an audio deferral that does not include the health information that was requested.

Clause 2: In addition to the method of clause 1, wherein the request includes a reminder time at which to provide the health information in the future, and wherein the AI assistant device identifies whether the unauthorized person is present in the environment with the requestor at the reminder time.

Clause 3: In addition to the method of clause 2, wherein the requestor is not present in the environment at the reminder time.

Clause 4: In addition to the method of clause 2 or 3, the method further comprises pairing a medication reminder with a non-medical reminder to be provided at the reminder time with the medication reminder when unauthorized persons are not present in the environment, and wherein the audio deferral outputs the non-medical reminder without the medication reminder.

Clause 5: In addition to the method of clause 2, 3, or 4, the method further comprises receiving, at the AI assistant device from the patient in an environment, a second utterance including a falsehood related to the health information, determining that the falsehood, when acted upon, would results in a medical harm to the patient, and generating, by the AI assistant device, a prophylactic confirmation audio that corrects the falsehood despite the unauthorized person being located in the environment.

Clause 6: In addition to the method of clauses 1, 2, 3, 4, or 5, wherein the audio deferral requests confirmation from the patient or an authorized party with rights to authorize sharing of the health information whether to share the health information while the unauthorized person is in the environment or reclassify the unauthorized person to be permitted to receive the health information.

Clause 7: In addition to the method of clauses 1, 2, 3, 4, 5, or 6, the method further comprises after generating the audio deferral, providing the a reply to the requestor that includes the health information via a video device linked with the assistant device as an alternative channel.

Clause 8: In addition to the method of clauses 1, 2, 3, 4, 5, 6, or 7, wherein the requestor is the unauthorized person.

Clause 9: In addition to the method of clauses 1, 2, 3, 4, 5, 6, 7, or 8, wherein the requestor is the patient.

Clause 10: In addition to the method of clauses 1, 2, 3, 4, 5, 6, 7, 8, or 9, the method further comprising in response to determining that the request is directed from the requestor to the patient or an authorized party to share the health information, waiting for a predefined time for a reply before confirming whether the unauthorized person is present in the environment.

Clause 11: A method comprising receiving, at an Artificial Intelligence (AI) assistant device executing a local instance of machine learning model, a request for health information related to a patient from a requestor in an environment, in response to determining via the machine learning model that the request is directed from the requestor to the patient or an authorized party to share the health information, waiting for a predefined time for a reply; after the predefined time, in response to the patient or the authorized party not sharing the health information: confirming whether an unauthorized person is present in the environment with the AI assistant device via the machine learning model, wherein the unauthorized person is not permitted by the patient to receive the health information; in response to confirming that the unauthorized person is not present in the environment, determining whether the reply included the health information requested by the request; and when the reply did not include the health information, generating an audio alert by the AI assistant device that includes the health information requested by the request.

Clause 12: The method of clause 11, wherein the patient does not share the health information with the requestor by providing an utterance that includes a falsehood, further comprising: receiving the utterance; performing speech recognition on the utterance; comparing contents of the utterance against the health information; and in response to the contents not matching the health information, determining that the utterance includes the falsehood.

Clause 13: The method of clause 12, the method further comprising: identifying that the falsehood relates to a medication for the patient; determining that the medication, when administered according to the falsehood, results in a medical harm to the patient; and wherein the audio alert is a prophylactic confirmation audio that corrects the falsehood.

Clause 14: The method of clauses 11, 12, or 13, wherein the patient does not share the health information with the requestor by not providing the reply with the health information before the predefined time.

Clause 15: The method of clauses 11, 12, 13, or 14, the method further comprising receiving, at the AI assistant device from the requestor in the environment, a second request for second health information related to the patient, in response to determining that the second request is directed from the requestor to the patient or the authorized party to share the health information, waiting for the predefined time for a second reply, receiving a first utterance from the patient or the authorized party, receiving a second utterance including a confirmation query from the requestor, determining whether the first utterance includes the second health information, and when the first utterance includes the second health information, generating an audio confirmation by the AI assistant device that the first utterance includes the second health information requested by the second request.

Clause 16: The method of clauses 11, 12, 13, 14, or 15, wherein confirming whether the unauthorized person is present in the environment with the AI assistant device further comprises determining a number of persons in the environment via at least one a motion sensor, a camera sensor, an entry sensor, or a microphone, identifying each person in the environment based on one or more of: facial recognition, voice recognition; and, interpersonal identification via speech recognition; and in response to the number of persons in the environment equaling a number of persons identified in the environment and each person therein being identified as one or the patient or an authorized person, confirming that no unauthorized persons are present in the environment with the AI assistant device.

Clause 17: An Artificial Intelligence (AI) assistant device comprising a processor; and a memory, including instructions for a machine learning model that when executed by the processor cause the processor to perform operations comprising: receiving, at an AI assistant device from a requestor in an environment, an utterance including a request to provide health information related to a patient, determining, via the machine learning model, whether an unauthorized person is present in the environment with the AI assistant device, wherein the unauthorized person is not permitted by the patient to receive the health information but is permitted to interact with the AI assistant device, and in response to determining that the unauthorized person is present, generating, by the AI assistant device, an audio deferral that does not include the health information that was requested.

Clause 18: The AI assistant device of clause 17, wherein the AI assistant device is in communication with sensors in the environment, including at least one of a motion sensor, a camera, or an entry sensor to confirm whether the unauthorized person is present, wherein confirming whether the unauthorized person is present further comprises: determining a number of persons in the environment, identifying each person in the environment based on one or more of: facial recognition; voice recognition; and interpersonal identification via speech recognition; and in response to the number of persons in the environment equaling a number of persons identified in the environment and each person identified being identified as one or the patient or an authorized person, confirming that no unauthorized persons are present in the environment with the AI assistant device.

Clause 19: The AI assistant device of clause 17 or 18, wherein the AI assistant device is in communication with remote computing resources that perform speech recognition of the utterance on behalf of the AI assistant device.

Clause 20: The AI assistant device of clause 17, 18, or 19, wherein the AI assistant device locally caches a subset of health records including medication schedules, upcoming doctor appointments scheduled within a first predefined window, and previous medical services received within a second predefined window.

What is claimed is:
1. A method, comprising:
receiving, at an Artificial Intelligence (AI) assistant device from a requestor in an environment, an utterance including a request to provide health information related to a patient;
confirming, via a machine learning model hosted by the AI assistant device, whether an unauthorized person is present in the environment with the AI assistant device, wherein the unauthorized person is not permitted by the patient to receive the health information but is permitted to interact with the AI assistant device, wherein the request includes a reminder time at which to provide the health information in the future, and wherein the AI assistant device identifies whether the unauthorized person is present in the environment with the requestor at the reminder time;
in response to determining, via the machine learning model, that the request is directed from the requestor to the patient or an authorized party to share the health information, waiting for a predefined time for a reply before confirming whether the unauthorized person is present in the environment; and
in response to determining that the unauthorized person is present, generating, by the AI assistant device, an audio deferral that does not include the health information that was requested.

2. The method of claim 1, wherein the requestor is not present in the environment at the reminder time.

3. The method of claim 1, further comprising:
pairing a medication reminder with a non-medical reminder to be provided at the reminder time with the medication reminder when unauthorized persons are not present in the environment; and
wherein the audio deferral outputs the non-medical reminder without the medication reminder.

4. The method of claim 1, further comprising:
receiving, at the AI assistant device from the patient in an environment, a second utterance including a falsehood related to the health information;
determining that the falsehood, when acted upon, would results in a medical harm to the patient; and
generating, by the AI assistant device, a prophylactic confirmation audio that corrects the falsehood despite the unauthorized person being located in the environment.

5. The method of claim 1, wherein the audio deferral requests confirmation from the patient or an authorized party with rights to authorize sharing of the health information whether to share the health information while the unauthorized person is in the environment or reclassify the unauthorized person to be permitted to receive the health information.

6. The method of claim 1, further comprising:
after generating the audio deferral, providing the reply to the requestor that includes the health information via a video device linked with the AI assistant device as an alternative channel.

7. The method of claim 1, wherein the requestor is the unauthorized person.

8. The method of claim 1, wherein the requestor is the patient.

9. A method, comprising:
receiving, at an Artificial Intelligence (AI) assistant device executing a local instance of machine learning model, a request for health information related to a patient from a requestor in an environment;
in response to determining via the machine learning model that the request is directed from the requestor to the patient or an authorized party to share the health information, waiting for a predefined time for a reply, wherein the patient or the authorized party does not share the health information with the requestor by not providing the reply with the health information before the predefined time;
after the predefined time, in response to the patient or the authorized party not sharing the health information:
confirming whether an unauthorized person is present in the environment with the AI assistant device via the machine learning model, wherein the unauthorized person is not permitted by the patient to receive the health information;
in response to confirming that the unauthorized person is not present in the environment, determining whether the reply included the health information requested by the requestor; and
when the reply did not include the health information, generating an audio alert by the AI assistant device that includes the health information requested by the request.

10. The method of claim 9, wherein the patient does not share the health information with the requestor by providing an utterance that includes a falsehood, further comprising:
receiving the utterance;
performing speech recognition on the utterance;
comparing contents of the utterance against the health information; and
in response to the contents not matching the health information, determining that the utterance includes the falsehood.

11. The method of claim 10, further comprising:
identifying that the falsehood relates to a medication for the patient; and
determining that the medication, when administered according to the falsehood, results in a medical harm to the patient,
wherein the audio alert is a prophylactic confirmation audio that corrects the falsehood.

12. The method of claim 9, further comprising:
receiving, at the AI assistant device from the requestor in the environment, a second request for second health information related to the patient;
in response to determining that the second request is directed from the requestor to the patient or the authorized party to share the health information, waiting for the predefined time for a second reply;
receiving a first utterance from the patient or the authorized party;
receiving a second utterance including a confirmation query from the requestor;
determining whether the first utterance includes the second health information; and
when the first utterance includes the second health information, generating an audio confirmation by the AI assistant device that the first utterance includes the second health information requested by the second request.

13. The method of claim 9, wherein confirming whether the unauthorized person is present in the environment with the AI assistant device further comprises:
determining a number of persons in the environment via at least one a motion sensor, a camera sensor, an entry sensor, or a microphone;
identifying each person in the environment based on one or more of:
facial recognition;
voice recognition; and
interpersonal identification via speech recognition; and
in response to the number of persons in the environment equaling a number of persons identified in the environment and each person therein being identified as one or the patient or an authorized person, confirming that no unauthorized persons are present in the environment with the AI assistant device.

14. An Artificial Intelligence (AI) assistant device, comprising:
a processor; and
a memory, including instructions for a machine learning model that when executed by the processor cause the processor to perform operations comprising:
receiving, at the AI assistant device from a requestor in an environment, an utterance including a request to provide health information related to a patient;
determining, via the machine learning model, whether an unauthorized person is present in the environment with the AI assistant device, wherein the unauthorized person is not permitted by the patient to receive the health information but is permitted to interact with the AI assistant device, wherein the request includes a reminder time at which to provide the health information in the future, and wherein the AI assistant device identifies whether the unauthorized person is present in the environment with the requestor at the reminder time;
in response to determining, via the machine learning model, that the request is directed from the requestor to the patient or an authorized party to share the health information, waiting for a predefined time for a reply before confirming whether the unauthorized person is present in the environment; and in response to determining that the unauthorized person is present, generating, by the AI assistant device, an audio deferral that does not include the health information that was requested.

15. The AI assistant device of claim 14, wherein the AI assistant device is in communication with sensors in the environment, including at least one of a motion sensor, a camera, or an entry sensor to confirm whether the unauthorized person is present, wherein confirming whether the unauthorized person is present further comprises:
- determining a number of persons in the environment;
- identifying each person in the environment based on one or more of:
  - facial recognition;
  - voice recognition; and
  - interpersonal identification via speech recognition; and
- in response to the number of persons in the environment equaling a number of persons identified in the environment and each person identified being identified as one or the patient or an authorized person, confirming that no unauthorized persons are present in the environment with the AI assistant device.

16. The AI assistant device of claim 14, wherein the AI assistant device is in communication with remote computing resources that perform speech recognition of the utterance on behalf of the AI assistant device.

17. The AI assistant device of claim 14, wherein the AI assistant device locally caches a subset of health records including medication schedules, upcoming doctor appointments scheduled within a first predefined window, and previous medical services received within a second predefined window.

* * * * *